US012698525B2

(12) United States Patent
Won et al.

(10) Patent No.: US 12,698,525 B2
(45) Date of Patent: Aug. 4, 2026

(54) DOUBLE-FUNCTIONAL OLIGONUCLEOTIDE COMPRISING COMPLEMENTARY NUCLEOTIDE SEQUENCE, MIS-MATCHED NUCLEOTIDE SEQUENCE, REPORTER, AND QUENCHER, AND A METHODS FOR NUCLEIC ACID AMPLIFICATION AND MEASUREMENT USING THE SAME

(71) Applicant: SD BIOSENSOR, INC., Suwon-si (KR)

(72) Inventors: Yoo Deok Won, Yongin-si (KR); Hae Joon Park, Seongnam-si (KR); Hyo Jin Seong, Yongin-si (KR); Sun Young Lee, Yongin-si (KR)

(73) Assignee: SD BIOSENSOR, INC., Suwon-si (KR)

( * ) Notice: Subject to any disclaimer, the term of this patent is extended or adjusted under 35 U.S.C. 154(b) by 934 days.

(21) Appl. No.: 17/354,730

(22) Filed: Jun. 22, 2021

(65) Prior Publication Data

US 2021/0381029 A1 Dec. 9, 2021

Related U.S. Application Data

(62) Division of application No. 15/577,242, filed as application No. PCT/KR2016/005517 on May 25, 2016, now abandoned.

(30) Foreign Application Priority Data

May 28, 2015 (KR) ........................ 10-2015-0074972

(51) Int. Cl.
*C12Q 1/68* (2018.01)
*C12Q 1/686* (2018.01)
(52) U.S. Cl.
CPC .............. *C12Q 1/686* (2013.01); *C12Q 1/68* (2013.01)
(58) Field of Classification Search
CPC ...................................................... C12Q 1/686
See application file for complete search history.

(56) References Cited

U.S. PATENT DOCUMENTS

| | | | | |
|---|---|---|---|---|
| 10,619,198 B2 * | 4/2020 | Won | ..................... | C12Q 1/6848 |
| 2006/0188902 A1 * | 8/2006 | Narayanan | ........... | C12Q 1/6816 |
| | | | | 536/25.32 |
| 2011/0311968 A1 * | 12/2011 | Will | ..................... | C12Q 1/6858 |
| | | | | 435/194 |
| 2012/0264643 A1 * | 10/2012 | Chun | ................... | C12Q 1/6816 |
| | | | | 435/6.12 |
| 2016/0115526 A1 * | 4/2016 | Fu | .......................... | C12Q 1/686 |
| | | | | 702/19 |
| 2018/0187240 A1 * | 7/2018 | Won | ....................... | C12Q 1/686 |
| 2021/0381029 A1 * | 12/2021 | Won | ........................ | C12Q 1/68 |

FOREIGN PATENT DOCUMENTS

| | | | | |
|---|---|---|---|---|
| KR | 101742681 B1 * | 6/2017 | ............... | C12Q 1/68 |
| WO | WO-2008063194 A1 * | 5/2008 | ........... | C12Q 1/6823 |
| WO | WO-2016122135 A1 * | 8/2016 | ............... | C12Q 1/68 |
| WO | WO-2016190654 A1 * | 12/2016 | ............... | C12Q 1/68 |

OTHER PUBLICATIONS

English Translation of KR-10-20150015276. published Jun. 1, 2017. (Year: 2017).*
KR-10-2015-0015276 by Won et al. pub. Jun. 1, 2017, filed Jan. 30, 2015. (Year: 2017).*
Chun et al., 2007. Dual priming oligonucleotide system for the multiplex detection of respiratory viruses and SNP genotyping of CYP2C19 gene. Nucleic acids research, 35(6), e40, pp. 1-6. (Year: 2007).*
Hazbon et al., 2004. Hairpin primers for simplified single-nucleotide polymorphism analysis of *Mycobacterium tuberculosis* and other organisms. Journal of clinical microbiology, 42(3), pp. 1236-1242. (Year: 2004).*
Hwang et al., 2003. Annealing control primer system for improving specificity of PCR amplification. Biotechniques, 35(6), pp. 1180-1184. (Year: 2003).*

(Continued)

*Primary Examiner* — Gary Benzion
*Assistant Examiner* — Olayinka A Oyeyemi
(74) *Attorney, Agent, or Firm* — Harvest IP Law, LLP

(57) ABSTRACT

The present disclosure relates to a complementary double-stranded oligo, in which, for the amplification of a particular gene sequence, an inosine linker is linked to the 5'-terminus of a primer for the corresponding sequence, a sequence complementary to the primer is linked to the inosine linker, and at least one mis-matched nucleotide is included in the complementary sequence to form a bubble structure; in which, depending on the treatment temperature, at a prede-termined temperature or lower, a single stranded oligo is turned into a double-stranded form to exist in an inactivation form, and at a predetermined temperature or higher, the oligo is activated into a single-stranded oligo; and in which, a fluorescent substance (reporter dye) and a quenching material (quencher molecule) are attached to the oligo, so that the oligo can be applied as a primer or a probe, and thus only two oligos can realize the gene amplification and fluorescent signal real-time measurement with high speci-ficity, and to a measuring method after a fluorescent arrange-ment step using the oligomer is added. The present disclo-sure has advantages in view of an oligo and a design method therefor, in which an oligo capable of simultaneously per-forming amplification and detection with an amplification size of 500 bp to 1000 bp for a particular gene is used to allow a reporter dye and a quencher molecule to be attached to only two target gene amplification sites, thereby confirm-ing whether real-time amplification occurs.

7 Claims, 17 Drawing Sheets

Specification includes a Sequence Listing.

(56) References Cited

OTHER PUBLICATIONS

Kutyavin, I.V., 2010. New approach to real-time nucleic acids detection: folding polymerase chain reaction amplicons into a secondary structure to improve cleavage of Förster resonance energy transfer probes in 5'-nuclease assays. Nucleic acids research, 38(5), e29, pp. 1-12. (Year: 2010).*

Li et al., 2021. A novel fluorescent FRET hairpin probe switch for aflD gene detection in real fermented soybean paste. Food Analytical Methods, 14, pp. 2469-2477. (Year: 2021).*

Takei et al., 2014. Detection of hepatitis C virus by single-step hairpin primer RT-PCR. Bioorganic & Medicinal Chemistry Letters, 24(1), pp. 394-396. (Year: 2014).*

KR-101742681_Decsription is the English Translation of KR-10742681B1,pp. 1-9, published Jun. 1, 2017, filed Jan. 30, 2015. (Year: 2017).*

* cited by examiner

| | Cont. Tat.P | Fam01 | Fam02 | Fam04 | Fam05 | Fam07 | Fam08 | Fam09 | Fam15 | Fam17 | Fam21 |
|---|---|---|---|---|---|---|---|---|---|---|---|
| 95°C,65°C | 13000 | 65000 | 65000 | 65000 | 53000 | 65000 | 65000 | 65000 | 65000 | 65000 | 65000 |
| 95°C,45°C | 10000 | 10000 | 17000 | 32000 | 12000 | 20000 | 20000 | 20000 | 65000 | 65000 | 65000 |
| 95°C,25°C | 10000 | 10000 | 10000 | 10000 | 12000 | 18000 | 18000 | 18000 | 65000 | 65000 | 65000 |

FIG. 3

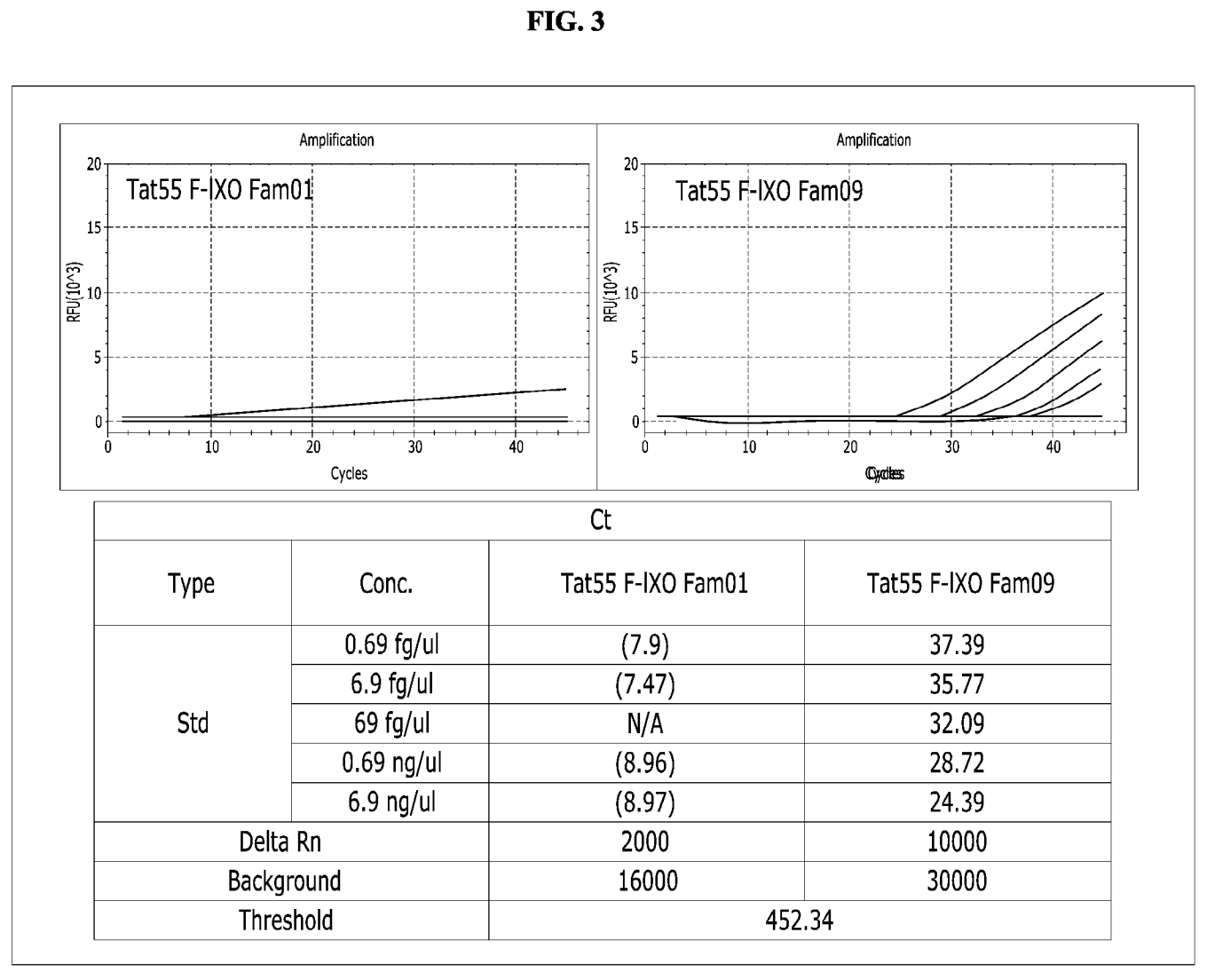

| Type | | Conc. | Ct | |
|---|---|---|---|---|
| | | | Tat55 F-IXO Fam01 | Tat55 F-IXO Fam09 |
| Std | | 0.69 fg/ul | (7.9) | 37.39 |
| | | 6.9 fg/ul | (7.47) | 35.77 |
| | | 69 fg/ul | N/A | 32.09 |
| | | 0.69 ng/ul | (8.96) | 28.72 |
| | | 6.9 ng/ul | (8.97) | 24.39 |
| Delta Rn | | | 2000 | 10000 |
| Background | | | 16000 | 30000 |
| Threshold | | | 452.34 | |

FIG. 4

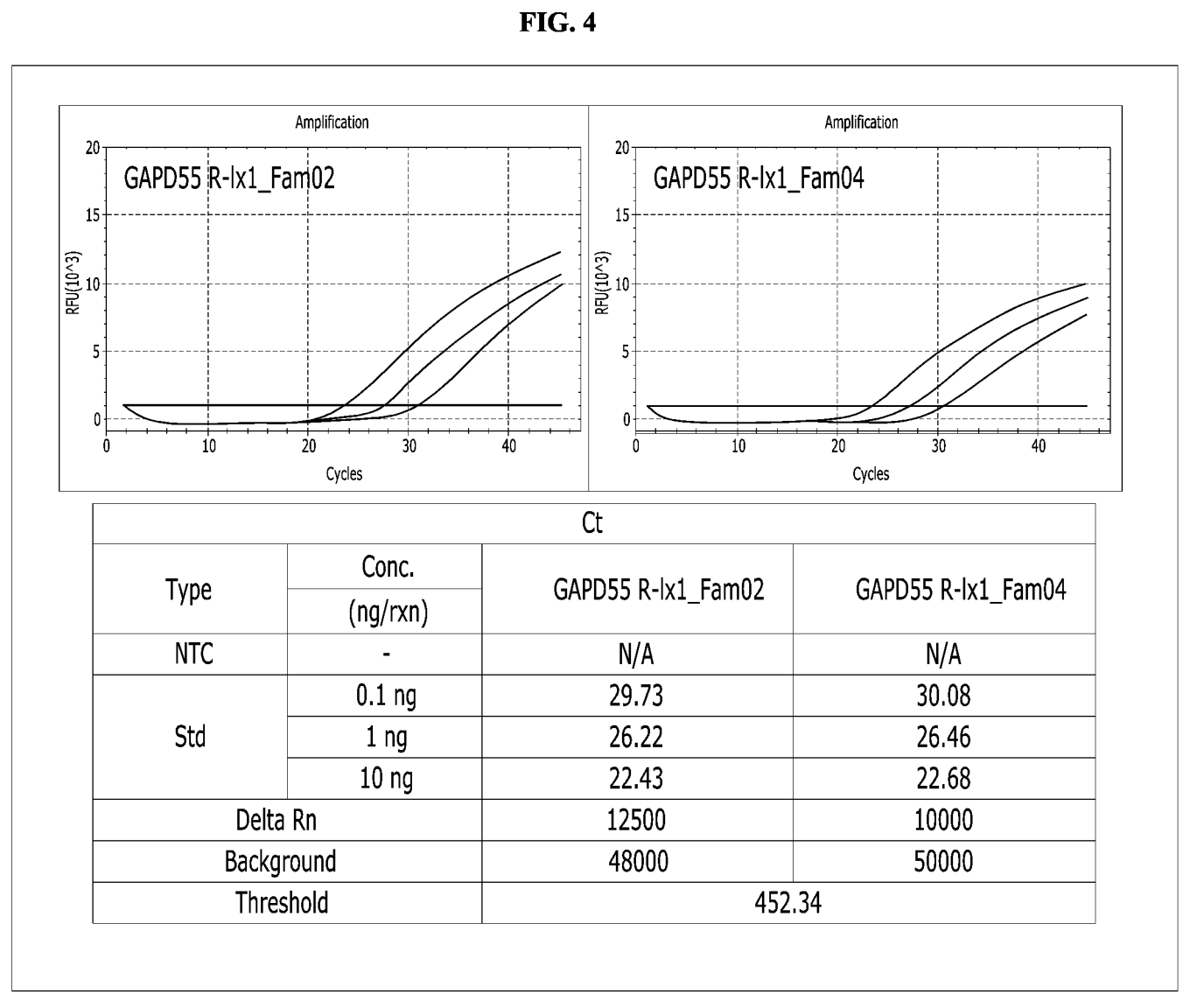

| Type | Conc. (ng/rxn) | Ct | |
| --- | --- | --- | --- |
| | | GAPD55 R-lx1_Fam02 | GAPD55 R-lx1_Fam04 |
| NTC | - | N/A | N/A |
| Std | 0.1 ng | 29.73 | 30.08 |
| | 1 ng | 26.22 | 26.46 |
| | 10 ng | 22.43 | 22.68 |
| Delta Rn | | 12500 | 10000 |
| Background | | 48000 | 50000 |
| Threshold | | 452.34 | |

| | | Ct | | |
|---|---|---|---|---|
| | | 95°C,65°C,45°C | 95°C,55°C,45°C | 95°C,45°C,45°C |
| Type | Conc.<br>(ng/rxn) | B-actin 55°C F | B-actin 55°C F | B-actin 55°C F |
| NTC | - | N/A | N/A | N/A |
| Std | 0.125 | 35.23 | 36.78 | 37.02 |
| | 1.25 | 31.25 | 32.47 | 33.10 |
| | 12.5 | 27.30 | 27.90 | 28.60 |
| Delta Rn | | 28000 | 25000 | 22000 |
| Background | | 8000 | 9000 | 9000 |
| Threshold | | | 805.13 | |

FIG.9 (Continued)

Ct — Scanning Step #2)

| Type | Conc. (ng/rxn) | 10s,10s,10s | 30s,30s,30s |
|---|---|---|---|
| NTC | - | N/A | N/A |
| | 1.24 | 34.88 | 35.26 |
| | | 34.94 | 35.13 |
| Std | 12.4 | 31.85 | 31.35 |
| | | 31.97 | 31.52 |
| | 124 | 29.48 | 29.03 |
| | | 29.33 | 28.32 |
| Delta Rn | | 19000 | 23000 |
| Background | | 7000 | 9000 |
| Threshold | | 805.13 | |

Ct — Non-Scanning Step

| Type | Conc. (ng/rxn) | 10s,10s | 30s,30s |
|---|---|---|---|
| NTC | - | N/A | N/A |
| | 1.24 | 35.28 | 35.36 |
| | | 35.43 | 35.11 |
| Std | 12.4 | 31.88 | 32.03 |
| | | 31.89 | 32.41 |
| | 124 | 29.13 | 29.47 |
| | | 29.03 | 29.63 |
| Delta Rn | | 20000 | 15000 |
| Background | | 15000 | 11000 |
| Threshold | | 805.13 | |

FIG.10

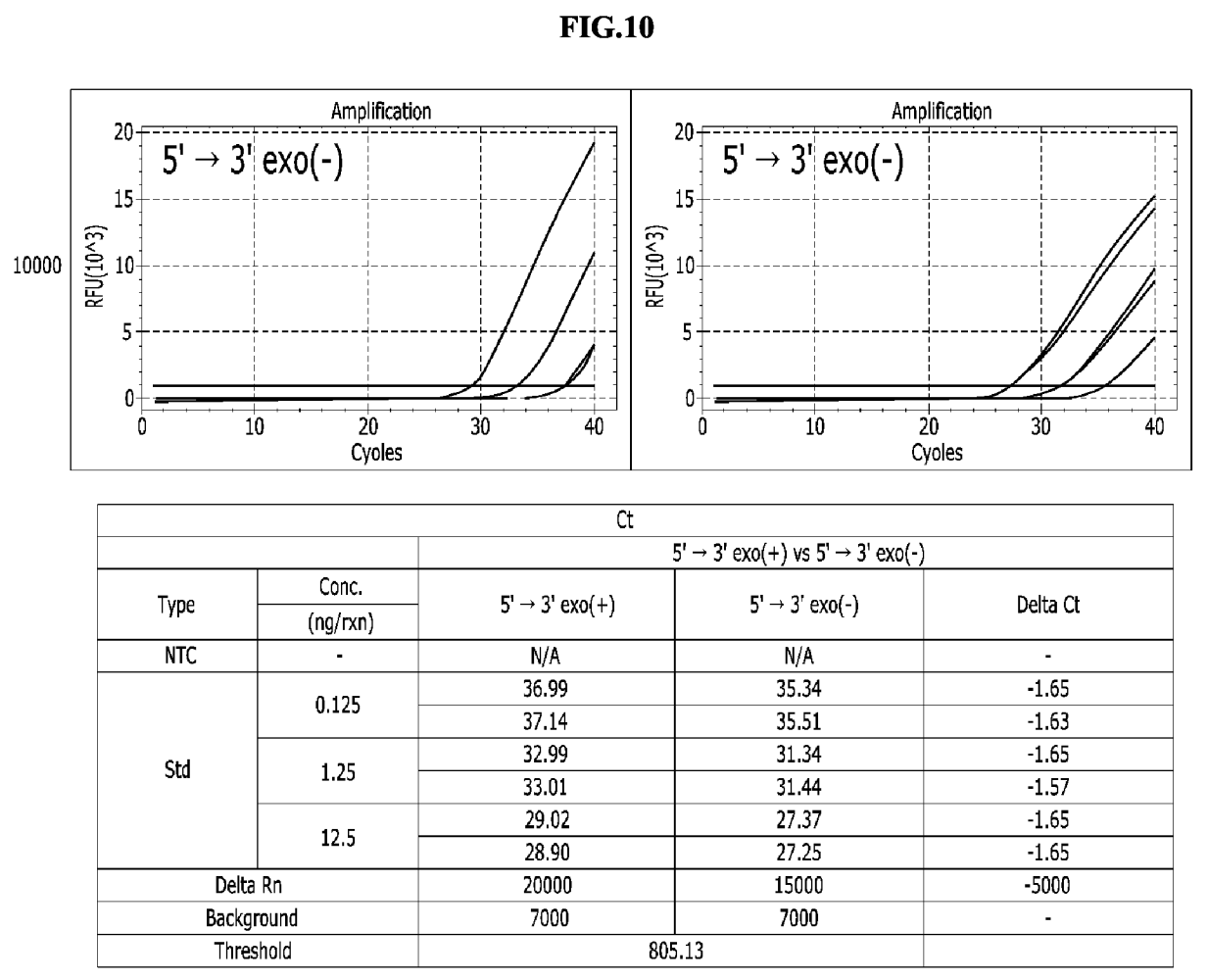

| Type | Conc. (ng/rxn) | Ct | | Delta Ct |
|---|---|---|---|---|
| | | 5' → 3' exo(+) vs 5' → 3' exo(-) | | |
| | | 5' → 3' exo(+) | 5' → 3' exo(-) | |
| NTC | - | N/A | N/A | - |
| Std | 0.125 | 36.99 | 35.34 | -1.65 |
| | | 37.14 | 35.51 | -1.63 |
| | 1.25 | 32.99 | 31.34 | -1.65 |
| | | 33.01 | 31.44 | -1.57 |
| | 12.5 | 29.02 | 27.37 | -1.65 |
| | | 28.90 | 27.25 | -1.65 |
| Delta Rn | | 20000 | 15000 | -5000 |
| Background | | 7000 | 7000 | - |
| Threshold | | 805.13 | | |

| | | B-actin 55°C F DFO +gDNA conventional primer | | | | | | |
|---|---|---|---|---|---|---|---|---|
| | Ct | | | | | | | |
| Type | Conc. (ng/rxn) | 50 bp | 216 bp | 300 bp | 450 bp | 800 bp | 1000 bp | |
| NTC | - | N/A | N/A | N/A | N/A | N/A | N/A | |
| Std | 1/1000X | 34.72 | 36.6 | 34.13 | 37.11 | 38.13 | 35.12 | |
| | 1/100X | 30.37 | 33.38 | 32.02 | 33.57 | 33.40 | 32.39 | |
| | 1/10X | 28.42 | 30.17 | 29.16 | 31.00 | 30.90 | 29.05 | |
| Delta Rn | | 21000 | 20000 | 18000 | 12000 | 16000 | 14000 | |
| Background | | | | | 7000 | | | |
| Threshold | | | | | 805.13 | | | |

FIG.12

| | Conc. | TaqMan cont. | DFO systems | | |
| | | | B-actin55 F-IX1 Fam05 | B-actin55 R-B IX1 Fam05 | B-actin55 IX1 [F+R]-B |
|---|---|---|---|---|---|
| | (ng/rxn) | | | | |
| NTC | - | N/A | N/A | N/A | N/A |
| Std | 1.25 | 31.23 | 31.97 | 32.84 | 33.54 |
| | 12.5 | 27.17 | 28.00 | 28.33 | 29.27 |
| | 125 | 23.70 | 23.78 | 23.27 | 23.96 |
| Delta Rn | | 12500 | 28000 | 25000 | 40000 |
| Background | | 6000 | 7000 | 12000 | 14000 |
| Threshold | | | 805.13 | | |

FIG.14

| Ct | | | | | | | |
|---|---|---|---|---|---|---|---|
| | | TaqMan control | | | DFO systems | | |
| Type | Conc. (ng/rxn) | FAM(B-actin) | HEX (Tat) | CY5(M13) | FAM(B-actin) | HEX (Tat) | CY5(M13) |
| NTC | - | N/A | N/A | N/A | N/A | N/A | N/A |
| | | N/A | N/A | N/A | N/A | N/A | N/A |
| Std | 1/10X | 29.13 | 27.88 | 28.27 | 29.44 | 30.01 | 29.31 |
| | | 29.10 | 27.86 | 28.56 | 29.32 | 29.95 | 29.23 |
| | 1x | 25.45 | 24.30 | 24.81 | 25.66 | 26.16 | 25.55 |
| | | 25.68 | 24.64 | 25.25 | 25.85 | 25.71 | 25.68 |
| Delta Rn | | 2000 | 1800 | 1700 | 4400 | 180 | 3000 |
| Background | | 3000 | 2700 | 3000 | 4000 | 4000 | 3000 |
| Threshold | | 100 | | | | | |

SEQUENCE LISTING

```
<110> SD Biosensor, INC.

<120> DOUBLE-FUNCTIONAL OLIGONUCLEOTIDE COMPRISING COMPLEMENTARY
      NUCLEOTIDE SEQUENCE, MIS-MATCHED NUCLEOTIDE SEQUENCE, REPORTER,
      AND QUENCHER, AND A METHODS FOR NUCLEIC ACID AMPLIFICATION AND
      MEASUREMENT USING THE SAME

<130> SDPCT1

<150> KR 10-2015-0074972

<151> 2015-05-28

<160> 33

<170> PatentIn version 3.5

<210> 1

<211> 27

<212> DNA

<213> Artificial Sequence

<220>

<223> Tat P

<400> 1
gccctggaag catccaggaa gtcagcc                                    27

<210> 2

<211> 50

<212> DNA

<213> Artificial Sequence

<220>

<223> Tat55 F-Ix0_Fam01

<400> 2
attctgctta caactgaccc aattcgaatt gggtgtcaac atagcagaat           50

<400> 6
attctgctta caactgaccc aattcgaatt gggtgtcaac atagcagaat           50

<210> 7

<211> 43

<212> DNA

<213> Artificial Sequence

<220>

<223> GAPD55 R-Ix1_Fam02

<220>

<221> modified_base
```

-continued

| SEQUENCE LISTING |
|---|

```
<222> (22)

<223> n is inosine

<400> 7
tacagcatgt cccacgtggg antcccacca ccctgttgct gta          43

<210> 8

<211> 43

<212> DNA

<213> Artificial Sequence

<220>

<223> GAPD55 R-Ix1_Fam04

<220>

<221> modified_base

<222> (22)

<223> n is inosine

<400> 8
tacagcatgt cccacgtggg antcccacca ccctgttgct gta          43

<210> 9

<211> 43

<212> DNA

<213> Artificial Sequence

<220>

<210> 3

<211> 50

<212> DNA

<213> Artificial Sequence

<220>

<223> Tat55 F-Ix0_Fam15

<400> 3
attctgctta caactgaccc aattcgaatt gggtgtcaac atagcagaat          50

<210> 4

<211> 50

<212> DNA

<213> Artificial Sequence

<220>

<223> Tat55 F-Ix0_Fam15

<400> 4
attctgctta caactgaccc aattcgaatt gggtgtcaac atagcagaat          50

<210> 5

<211> 50
```

-continued

SEQUENCE LISTING

<212> DNA

<213> Artificial Sequence

<220>

<223> Tat55 F-Ix0_Fam17

<400> 5
attctgctta caactgaccc aattcgaatt gggtgtcaac atagcagaat          50

<210> 6

<211> 50

<212> DNA

<213> Artificial Sequence

<220>

<223> Tat55 F-Ix0_Fam21

<223> GAPD55 R-Ix1_Fam07

<220>

<221> modified_base

<222> (22)

<223> n is inosine

<400> 9
tacagcatgt cccacgtggg antcccacca ccctgttgct gta          43

<210> 10

<211> 43

<212> DNA

<213> Artificial Sequence

<220>

<223> GAPD55 R-Ix1_Fam08

<220>

<221> modified_base

<222> (22)

<223> n is inosine

<400> 10
tacagcatgt cccacgtggg antcccacca ccctgttgct gta          43

<210> 11

<211> 41

<212> DNA

<213> Artificial Sequence

<220>

<223> B-actin55 F-Ix1_Fam05

<220>

<221> modified_base

SEQUENCE LISTING

<222> (21)

<223> n is inosine

<400> 11
aagcagcgca ccgcatctct nagagatggc cacggctgct t                    41

<210> 12

<211> 41

<212> DNA

<213> Artificial Sequence

<220>

<223> B-actin65 F-Ix1_Fam05

<220>

<221> modified_base

<222> (21)

<223> n is inosine

<400> 12
aagcagccca ccccatctct nagagatggc cacggctgct t                    41

<210> 13

<211> 41

<212> DNA

<213> Artificial Sequence

<220>

<223> B-actin45 F-Ix1_Fam05

<220>

<221> modified_base

<222> (21)

<223> n is inosine

<400> 13
aagcacggca ccggatctct nagagatggc cacggctgct t                    41

<210> 14

<211> 19

<212> DNA

<213> Artificial Sequence

<220>

<223> B-actin R_B

<400> 14
cggatgtcca cgtcacact                                             19

<210> 15

<211> 21

-continued

| SEQUENCE LISTING |
| --- |

<212> DNA

<213> Artificial Sequence

<220>

<223> B-actin_R-gDNA-3

<400> 15
ggaaatgagg gcaggactta g                                    21

<210> 16

<211> 20

<212> DNA

<213> Artificial Sequence

<220>

<223> actin_R-gDNA-50-2

<400> 16
gctcgtagct cttctccagg                                      20

<210> 17

<211> 19

<212> DNA

<213> Artificial Sequence

<220>

<223> actin R-gDNA-300-3

<400> 17
gtctttgcgg atgtccacg                                       19

<210> 18

<211> 18

<212> DNA

<213> Artificial Sequence

<220>

<223> actin_R-gDNA-450-3

<400> 18
gaccctggat gtgacagc                                        18

<210> 19

<211> 18

<212> DNA

<213> Artificial Sequence

<220>

<223> actin R-gDNA-800-3

<400> 19
accgactgct gtcacctt                                        18

<210> 20

-continued

| SEQUENCE LISTING |
| --- |

<211> 19

<212> DNA

<213> Artificial Sequence

<220>

<223> actin_R-gDNA-1000-1

<400> 20
tggacttggg agaggactg                                          19

<210> 21

<211> 20

<212> DNA

<213> Artificial Sequence

<220>

<223> B-actin F

<400> 21
agagatggcc acggctgctt                                         20

<210> 22

<211> 39

<212> DNA

<213> Artificial Sequence

<220>

<223> actin55R_B-Ix1Fam05

<220>

<221> modified_base

<222> (20)

<223> n is inosine

<400> 22
agtgtgacca ccacatccgn cggatgtcca cgtcacact                    39

<210> 23

<211> 22

<212> DNA

<213> Artificial Sequence

<220>

<223> Tat R-2

<400> 23
gcaatagcaa gtggtacaag ca                                      22

<210> 24

<211> 20

<212> DNA

-continued

| SEQUENCE LISTING |
| --- |

<213> Artificial Sequence

<220>

<223> GAPD N_F-2

<400> 24
aggaccaggt tgtctcctgt                                              20

<210> 25

<211> 22

<212> DNA

<213> Artificial Sequence

<220>

<223> B-actin_P

<400> 25
agcggttccg ctgccctgag gc                                           22

<210> 26

<211> 51

<212> DNA

<213> Artificial Sequence

<220>

<223> Tat55 F-Ix1_Hex09

<220>

<221> modified_base

<222> (26)

<223> n is inosine

<400> 26
attctgctta caactgaccc aattengaat tgggtgtcaa catagcagaa t       51

<210> 27

<211> 25

<212> DNA

<213> Artificial Sequence

<220>

<223> Tat F

<400> 27
gaattgggtg tcaacatagc agaat                                        25

<210> 28

<211> 22

<212> DNA

<213> Artificial Sequence

<220>

<223> Tat R-4

-continued

---

SEQUENCE LISTING

---

<400> 28
acttggcaat gaaagcaaca tc                                    22

<210> 29

<211> 27

<212> DNA

<213> Artificial Sequence

<220>

<223> Tat P_Hex

<400> 29
gccctggaag catccaggaa gtcagcc                               27

<210> 30

<211> 18

<212> DNA

<213> Artificial Sequence

<220>

<223> M13_F-3

<400> 30
gctaccctcg ttccgatg                                         18

<210> 31

<211> 19

<212> DNA

<213> Artificial Sequence

<220>

<223> M13_R-3

<400> 31
cgccgacaat gacaacaac                                        19

<210> 32

<211> 22

<212> DNA

<213> Artificial Sequence

<220>

<223> M13_P-2

<400> 32
cctgcaagcc tcagcgaccg aa                                    22

<210> 33

<211> 37

<212> DNA

<213> Artificial Sequence

---
SEQUENCE LISTING
---

<220>

<223> M13 F-3_Fam

<220>

<221> modified_base

<222> (19)

<223> n is inosine

<400> 33
catcggttgc tgggtagong ctaccctcgt tccgatg

---

---
SEQUENCE LISTING
---

<160> NUMBER OF SEQ ID NOS: 33

<210> SEQ ID NO 1
<211> LENGTH: 27
<212> TYPE: DNA
<213> ORGANISM: Artificial Sequence
<220> FEATURE:
<223> OTHER INFORMATION: Tat P

<400> SEQUENCE: 1
gccctggaag catccaggaa gtcagcc                                         27

<210> SEQ ID NO 2
<211> LENGTH: 50
<212> TYPE: DNA
<213> ORGANISM: Artificial Sequence
<220> FEATURE:
<223> OTHER INFORMATION: Tat55 F-Ix0_Fam01

<400> SEQUENCE: 2
attctgctta caactgaccc aattcgaatt gggtgtcaac atagcagaat              50

<210> SEQ ID NO 3
<211> LENGTH: 50
<212> TYPE: DNA
<213> ORGANISM: Artificial Sequence
<220> FEATURE:
<223> OTHER INFORMATION: Tat55 F-Ix0_Fam15

<400> SEQUENCE: 3
attctgctta caactgaccc aattcgaatt gggtgtcaac atagcagaat              50

<210> SEQ ID NO 4
<211> LENGTH: 50
<212> TYPE: DNA
<213> ORGANISM: Artificial Sequence
<220> FEATURE:
<223> OTHER INFORMATION: Tat55 F-Ix0_Fam15

<400> SEQUENCE: 4
attctgctta caactgaccc aattcgaatt gggtgtcaac atagcagaat              50

<210> SEQ ID NO 5
<211> LENGTH: 50
<212> TYPE: DNA
<213> ORGANISM: Artificial Sequence
<220> FEATURE:

-continued

<223> OTHER INFORMATION: Tat55 F-Ix0_Fam17

<400> SEQUENCE: 5
attctgctta caactgaccc aattcgaatt gggtgtcaac atagcagaat                    50

<210> SEQ ID NO 6
<211> LENGTH: 50
<212> TYPE: DNA
<213> ORGANISM: Artificial Sequence
<220> FEATURE:
<223> OTHER INFORMATION: Tat55 F-Ix0_Fam21

<400> SEQUENCE: 6
attctgctta caactgaccc aattcgaatt gggtgtcaac atagcagaat                    50

<210> SEQ ID NO 7
<211> LENGTH: 43
<212> TYPE: DNA
<213> ORGANISM: Artificial Sequence
<220> FEATURE:
<223> OTHER INFORMATION: GAPD55 R-Ix1_Fam02
<220> FEATURE:
<221> NAME/KEY: modified_base
<222> LOCATION: (22)
<223> OTHER INFORMATION: n is inosine

<400> SEQUENCE: 7
tacagcatgt cccacgtggg antcccacca ccctgttgct gta                          43

<210> SEQ ID NO 8
<211> LENGTH: 43
<212> TYPE: DNA
<213> ORGANISM: Artificial Sequence
<220> FEATURE:
<223> OTHER INFORMATION: GAPD55 R-Ix1_Fam04
<220> FEATURE:
<221> NAME/KEY: modified_base
<222> LOCATION: (22)
<223> OTHER INFORMATION: n is inosine

<400> SEQUENCE: 8
tacagcatgt cccacgtggg antcccacca ccctgttgct gta                          43

<210> SEQ ID NO 9
<211> LENGTH: 43
<212> TYPE: DNA
<213> ORGANISM: Artificial Sequence
<220> FEATURE:
<223> OTHER INFORMATION: GAPD55 R-Ix1_Fam07
<220> FEATURE:
<221> NAME/KEY: modified_base
<222> LOCATION: (22)
<223> OTHER INFORMATION: n is inosine

<400> SEQUENCE: 9
tacagcatgt cccacgtggg antcccacca ccctgttgct gta                          43

<210> SEQ ID NO 10
<211> LENGTH: 43
<212> TYPE: DNA
<213> ORGANISM: Artificial Sequence
<220> FEATURE:
<223> OTHER INFORMATION: GAPD55 R-Ix1_Fam08
<220> FEATURE:
<221> NAME/KEY: modified_base
<222> LOCATION: (22)
<223> OTHER INFORMATION: n is inosine

<400> SEQUENCE: 10

-continued

```
tacagcatgt cccacgtggg antcccacca ccctgttgct gta              43

<210> SEQ ID NO 11
<211> LENGTH: 41
<212> TYPE: DNA
<213> ORGANISM: Artificial Sequence
<220> FEATURE:
<223> OTHER INFORMATION: B-actin55 F-Ix1_Fam05
<220> FEATURE:
<221> NAME/KEY: modified_base
<222> LOCATION: (21)
<223> OTHER INFORMATION: n is inosine

<400> SEQUENCE: 11
aagcagcgca ccgcatctct nagagatggc cacggctgct t                41

<210> SEQ ID NO 12
<211> LENGTH: 41
<212> TYPE: DNA
<213> ORGANISM: Artificial Sequence
<220> FEATURE:
<223> OTHER INFORMATION: B-actin65 F-Ix1_Fam05
<220> FEATURE:
<221> NAME/KEY: modified_base
<222> LOCATION: (21)
<223> OTHER INFORMATION: n is inosine

<400> SEQUENCE: 12
aagcagccca ccccatctct nagagatggc cacggctgct t                41

<210> SEQ ID NO 13
<211> LENGTH: 41
<212> TYPE: DNA
<213> ORGANISM: Artificial Sequence
<220> FEATURE:
<223> OTHER INFORMATION: B-actin45 F-Ix1_Fam05
<220> FEATURE:
<221> NAME/KEY: modified_base
<222> LOCATION: (21)
<223> OTHER INFORMATION: n is inosine

<400> SEQUENCE: 13
aagcacggca ccggatctct nagagatggc cacggctgct t                41

<210> SEQ ID NO 14
<211> LENGTH: 19
<212> TYPE: DNA
<213> ORGANISM: Artificial Sequence
<220> FEATURE:
<223> OTHER INFORMATION: B-actin R_B

<400> SEQUENCE: 14
cggatgtcca cgtcacact                                         19

<210> SEQ ID NO 15
<211> LENGTH: 21
<212> TYPE: DNA
<213> ORGANISM: Artificial Sequence
<220> FEATURE:
<223> OTHER INFORMATION: B-actin_R-gDNA-3

<400> SEQUENCE: 15
ggaaatgagg gcaggactta g                                      21

<210> SEQ ID NO 16
<211> LENGTH: 20
<212> TYPE: DNA
```

-continued

```
<213> ORGANISM: Artificial Sequence
<220> FEATURE:
<223> OTHER INFORMATION: actin_R-gDNA-50-2

<400> SEQUENCE: 16
gctcgtagct cttctccagg                                                        20

<210> SEQ ID NO 17
<211> LENGTH: 19
<212> TYPE: DNA
<213> ORGANISM: Artificial Sequence
<220> FEATURE:
<223> OTHER INFORMATION: actin_R-gDNA-300-3

<400> SEQUENCE: 17
gtctttgcgg atgtccacg                                                         19

<210> SEQ ID NO 18
<211> LENGTH: 18
<212> TYPE: DNA
<213> ORGANISM: Artificial Sequence
<220> FEATURE:
<223> OTHER INFORMATION: actin_R-gDNA-450-3

<400> SEQUENCE: 18
gaccctggat gtgacagc                                                          18

<210> SEQ ID NO 19
<211> LENGTH: 18
<212> TYPE: DNA
<213> ORGANISM: Artificial Sequence
<220> FEATURE:
<223> OTHER INFORMATION: actin_R-gDNA-800-3

<400> SEQUENCE: 19
accgactgct gtcacctt                                                          18

<210> SEQ ID NO 20
<211> LENGTH: 19
<212> TYPE: DNA
<213> ORGANISM: Artificial Sequence
<220> FEATURE:
<223> OTHER INFORMATION: actin_R-gDNA-1000-1

<400> SEQUENCE: 20
tggacttggg agaggactg                                                         19

<210> SEQ ID NO 21
<211> LENGTH: 20
<212> TYPE: DNA
<213> ORGANISM: Artificial Sequence
<220> FEATURE:
<223> OTHER INFORMATION: B-actin_F

<400> SEQUENCE: 21
agagatggcc acggctgctt                                                        20

<210> SEQ ID NO 22
<211> LENGTH: 39
<212> TYPE: DNA
<213> ORGANISM: Artificial Sequence
<220> FEATURE:
<223> OTHER INFORMATION: actin55R_B-Ix1Fam05
<220> FEATURE:
<221> NAME/KEY: modified_base
<222> LOCATION: (20)
<223> OTHER INFORMATION: n is inosine
```

<400> SEQUENCE: 22
agtgtgacca ccacatccgn cggatgtcca cgtcacact                          39

<210> SEQ ID NO 23
<211> LENGTH: 22
<212> TYPE: DNA
<213> ORGANISM: Artificial Sequence
<220> FEATURE:
<223> OTHER INFORMATION: Tat R-2

<400> SEQUENCE: 23
gcaatagcaa gtggtacaag ca                                            22

<210> SEQ ID NO 24
<211> LENGTH: 20
<212> TYPE: DNA
<213> ORGANISM: Artificial Sequence
<220> FEATURE:
<223> OTHER INFORMATION: GAPD N_F-2

<400> SEQUENCE: 24
aggaccaggt tgtctcctgt                                               20

<210> SEQ ID NO 25
<211> LENGTH: 22
<212> TYPE: DNA
<213> ORGANISM: Artificial Sequence
<220> FEATURE:
<223> OTHER INFORMATION: B-actin_P

<400> SEQUENCE: 25
agcggttccg ctgccctgag gc                                            22

<210> SEQ ID NO 26
<211> LENGTH: 51
<212> TYPE: DNA
<213> ORGANISM: Artificial Sequence
<220> FEATURE:
<223> OTHER INFORMATION: Tat55 F-Ix1_Hex09
<220> FEATURE:
<221> NAME/KEY: modified_base
<222> LOCATION: (26)
<223> OTHER INFORMATION: n is inosine

<400> SEQUENCE: 26
attctgctta caactgaccc aattcngaat tgggtgtcaa catagcagaa t            51

<210> SEQ ID NO 27
<211> LENGTH: 25
<212> TYPE: DNA
<213> ORGANISM: Artificial Sequence
<220> FEATURE:
<223> OTHER INFORMATION: Tat F

<400> SEQUENCE: 27
gaattgggtg tcaacatagc agaat                                         25

<210> SEQ ID NO 28
<211> LENGTH: 22
<212> TYPE: DNA
<213> ORGANISM: Artificial Sequence
<220> FEATURE:
<223> OTHER INFORMATION: Tat R-4

<400> SEQUENCE: 28

-continued

```
acttggcaat gaaagcaaca tc                                         22

<210> SEQ ID NO 29
<211> LENGTH: 27
<212> TYPE: DNA
<213> ORGANISM: Artificial Sequence
<220> FEATURE:
<223> OTHER INFORMATION: Tat P_Hex

<400> SEQUENCE: 29
gccctggaag catccaggaa gtcagcc                                    27

<210> SEQ ID NO 30
<211> LENGTH: 18
<212> TYPE: DNA
<213> ORGANISM: Artificial Sequence
<220> FEATURE:
<223> OTHER INFORMATION: M13_F-3

<400> SEQUENCE: 30
gctaccctcg ttccgatg                                              18

<210> SEQ ID NO 31
<211> LENGTH: 19
<212> TYPE: DNA
<213> ORGANISM: Artificial Sequence
<220> FEATURE:
<223> OTHER INFORMATION: M13_R-3

<400> SEQUENCE: 31
cgccgacaat gacaacaac                                             19

<210> SEQ ID NO 32
<211> LENGTH: 22
<212> TYPE: DNA
<213> ORGANISM: Artificial Sequence
<220> FEATURE:
<223> OTHER INFORMATION: M13_P-2

<400> SEQUENCE: 32
cctgcaagcc tcagcgaccg aa                                         22

<210> SEQ ID NO 33
<211> LENGTH: 37
<212> TYPE: DNA
<213> ORGANISM: Artificial Sequence
<220> FEATURE:
<223> OTHER INFORMATION: M13_F-3_Fam
<220> FEATURE:
<221> NAME/KEY: modified_base
<222> LOCATION: (19)
<223> OTHER INFORMATION: n is inosine

<400> SEQUENCE: 33
catcggttgc tgggtagcng ctaccctcgt tccgatg                         37
```

DOUBLE-FUNCTIONAL OLIGONUCLEOTIDE COMPRISING COMPLEMENTARY NUCLEOTIDE SEQUENCE, MIS-MATCHED NUCLEOTIDE SEQUENCE, REPORTER, AND QUENCHER, AND A METHODS FOR NUCLEIC ACID AMPLIFICATION AND MEASUREMENT USING THE SAME

CROSS-REFERENCE TO RELATED APPLICATION

This application is a divisional application of the U.S. application Ser. No. 15/577,242, filed Mar. 15, 2018, the disclosure of which is incorporated herein in its entirety by reference.

TECHNICAL FIELD

The present disclosure relates to a use of a double-functional oligonucleotide (hereinafter, "DFO") having both at least two bubble structures including a mis-matched nucleotide sequence in a complementary nucleotide sequence as an oligonucleotide including a complementary nucleotide sequence by linking an inosine linker at a 5'-terminus of a primer at a target gene specific site, and the functions of a primer and a probe as an oligonucleotide having reactivity according to the annealing temperature of a real-time polymerase chain reaction by placing the fluorescent substance, reporter, and extinction material, quencher, as a pair in the nucleotide sequence complementary to the 5'-terminus of this primer, the mis-matched sequence and the specific sequence of the target gene, and a method for nucleic acid amplification and measurement using the same.

BACKGROUND ART

Real-time PCR is an experimental method that can amplify a specific sequence in a DNA molecule and detect and measure the quantity in real time. In order to measure the amplified nucleic acid in real time, it requires buffers such as DNA polymerase, primer sets, dNTPs, and MgCl2, etc. which are basically necessary for polymerase chain reaction (PCR). In addition, a real-time gene amplification device capable of monitoring a fluorescent substance in real time and an intercalating dye such as SYBR GreenI, which is bound to a probe or amplified nucleic acid DNA including a fluorescent substance and a quenching material capable of confirming nucleic acid amplification, are essential. Accordingly, the structure and the experimental methods of the fluorescent substance and the probe including the same for the real-time PCR have been reported.

SYBR GreenI is a method to monitor the nucleic acid amplification by measuring the fluorescence after an extension step in the PCR process with a fluorescent dye that binds to double-stranded DNA. It is possible to conduct a monitor with a primer set that does not have a fluorescent substance attached as a substance of the real-time PCR, but it cannot be used for a simultaneous multiple test. Even if a dimer or a non-specific gene is amplified, fluorescence is detected, and thus a primer having high specificity should be used, and anti-Taq antibody should be used to reduce non-specific products (Morrison, T. B. et al., BioTechniques, 1998, 24:954-962). In order to overcome the disadvantages of such intercalating dyes, methods using a probe to which a fluorescent substance or a quenching material is attached are widely used.

As a method that is widely used for Real-Time PCR, there is a Taqman assay to which a hydrolysis probe is applied. The 5'3' exonuclease activity of Taq DNA polymerase and the fluorescence appear when a reporter, which is a fluorescent substance, and a quencher, which is a quenching material, are attached inside a primer set, and the distance between the two becomes farther away. If the distance is close, a probe that is subject to quenching is used. As the nucleic acid amplification reaction increases during the real-time PCR, the probe bound to a specific gene site emits light in a reporter as the distance of a quencher becomes farther away when a reporter dye attached to the 5'-terminus of the probe is released by 5'3' exonuclease action due to the polymerization reaction of Taq DNA polymerase, thereby occurring fluorescence detection (Livak, K. J., PCR Methods and Applications, 1998, 4:357-362). As such, the fluorescence sensitivity is determined by the distance between the reporter and the quencher and affects the sensitivity. In addition, there is a disadvantage in that the PCR efficiency is reduced when the length of the gene amplification product becomes longer from 63 bp for shortest length and 400 bp for longest length (Bustin, S. A. Journal of Molecular Endocrinology, 2000, 25:169-193).

The hybridization probe requires two primers and two probes for the PCR reaction. Along two probes, a probe near the 5'-terminus of the nucleic acid amplification product attaches an acceptor dye at the 3'-terminus and a probe near the 3'-terminus attaches a donor dye at the 5'-terminus for design. If two probes are located side by side in a specific site of the target gene, nucleic acid amplification monitoring can be achieved by detecting fluorescence in acceptor dyes (Wong, M. L, BioTechniques, 2005, 39:75-85). This method requires high homology site of the target gene for the use of two probes and has a disadvantage of high cost due to the use of two kinds of probes.

Hairpin probes include Molecular beacon in the type of stem-loop, Scorpion primer, Sunrise primer, and the like. Molecular beacon has a structure of stem-loop type. The loop part includes a complementary sequence to a specific site of the gene, and the stem part includes a complementary sequence so that the 5'-terminus and the 3'-terminus of the probe are bound. At each terminus, fluorescent substances and quenching materials are attached (Tyagi, S. and Kramer, R., Nature Biotechnology, 1996, 14:303-308). In the molecular beacon, the loop part is bound to a specific site of the gene, and the stem part is separated by the conformation transition, so that the distance between the fluorescent substance and the quenching material becomes distant and light emission occurs. In this process, if the stem part is designed too robust, the stem part will not be separated and no light emission will appear (Bustin, S. A. Journal of Molecular Endocrinology, 2000, 25:169-193). Scorpion primer has the function of a primer and a probe. When the complementary part of scorpion primer binds to a specific site of the gene and is subjected to an extension reaction and then single stranded by denaturation, the specific sequence of the target gene of the Scorpion primer binds to the extended sequence, and the distance between the fluorescent substance and the quenching material becomes distant and light emission appears. In the Taqman assay, a Scorpion primer is designed so that a primer would have a probe function without adding probes individually, and a complementary part and a specific sequence of the target gene are included so that specificity is high (Whitcombe, D., et. al., Nature Biotechnology, 1999, 17:804-807). As such, three parts of a specific sequence of the target gene are required, so that it is difficult to design a target gene having a low homology. The Sunrise primer is similar to the Scorpion primer and forms a hairpin loop at the 5'-terminus and has a sequence complementary to a specific sequence of the target gene at the 3'-terminus.

As the PCR process proceeds, the hairpin loop structure is elongated as it is extended by the opposite primer and light emission is performed (Wong, M. L., BioTechniques, 2005, 39:75-85). If the scorpion primer and the sunrise primer forming the hairpin loop at the 5' end as above are not denatured into a single strand by the temperature of the annealing and elongating stages, there is a problem that the fluorescence signal is not generated. Accordingly, the design for the hairpin loop is difficult and complicated so that the sequence site with a low homology has a restriction on the selection of a primer location according to the target gene sequence of many sites used to increase the specificity.

As a limiting condition for real-time PCR, intercalating dyes are detectable even when non-specific amplification occurs, and hydrolysis probes are limited in amplification size of target gene. In addition, there are disadvantages in that the design for a primer or a probe for detection of fluorescent dyes such as a hybridization probe, a hairpin probe, and the like is complicated and difficult.

PRIOR PATENT DOCUMENT

Korean Patent Laid-Open Publication No. 2003-0055343

DISCLOSURE

Technical Problem

The present disclosure has been designed to solve the above problems and invented in view of the above needs. It is an object of the present disclosure to provide an oligonucleotide, in which a complementary sequence of a primer to a target gene at the 5'-terminus links through a linker, a mis-matching sequence exists in a complementary sequence, and an annealing temperature can be controlled according to the number of sequences; in which the single strand oligonucleotide exists in an inactivation form in a double strand form at a predetermined temperature or lower, according to the processing temperature of an annealing and an extension, and in which a fluorescent substance (reporter dye) and a quenching material (quencher molecule) are attached to the oligonucleotide activated with a single strand oligonucleotide at a predetermined temperature or higher, so that the oligonucleotide can be applied as a primer or a probe, and thus two oligonucleotides can realize the gene amplification and fluorescent signal real-time measurement with high specificity because it can be designed only with the sequence for two locations of the target gene of forward and reverse primers and exist in an activated or inactivated state according to a specific temperature.

It is another object of the present disclosure to provide a method for real-time measurement of oligonucleotide and fluorescence signal in which the amplification size of a specific gene can be amplified and detected from 50 bp to 1000 bp simultaneously.

Technical Solution

In order to achieve the above object, the present disclosure provides a complementary double-stranded oligonucleotide, in which, for the amplification of a particular gene sequence, an inosine linker is linked to the 5'-terminus of a primer for the corresponding sequence, a sequence complementary to the primer is linked, and at least one mis-matched nucleotide is included in this site to form a bubble structure; and in which the oligonucleotide has a double-stranded structure including a pair of a reporter dye and a quencher molecule for detecting nucleic acid for specific gene amplification and is denatured into a single strand at a predetermined temperature or higher.

In the oligonucleotide of the present invention, oligonucleotides having a double-stranded structure at a specific temperature or below are preferable because a single-stranded oligonucleotide connects the primer site of the corresponding sequence of the specific gene and the complementary sequence thereof to the inosine linker, and oligonucleotides having a single-stranded structure are preferable at a specific temperature or higher, but not limited thereto.

In the oligonucleotides of the present invention, the mis-matching base sequence may be any one of adenine, guanine, cytosine, thymine, and uridine, and the number of nucleotides may be two or more, forming a bubble structure. It is preferable to be located in a complementary sequence of the primer to the sequence of the target gene.

It is preferable that the oligonucleotide of the present disclosure has two or more bubble structures in a linker site and a mis-matching site by linking a sequence complementary to the sequence of a target gene with a linker.

In an embodiment of the present invention, the inosine linker is preferably composed of 0 to 9 nucleotides, but is not limited thereto.

The oligonucleotide of the present disclosure attaches a reporter dye or a quencher molecule to the 5'-terminus and attaches a reporter dye or a quencher molecule from the 3'-terminus to the 5'-terminus direction at the 2nd location so that the distance between the reporter dye and the quencher molecule in a single-stranded structure is 15 mer or farther. In the double-stranded structure, the distance between the reporter dye and the quencher molecule is preferably within 14 mer, but is not limited thereto.

It is preferable to use oligonucleotides of the present disclosure and conventional primers as a set or a pair of oligonucleotides of the present disclosure as a set, and there is provided the use of DNA polymerase having 5'→3' exonuclease activity (+) or 5'→3' exonuclease inactivity (−). And there is provided a composition for real-time PCR using dNTPs, a buffer solution for reaction, and a set of the oligonucleotides.

As the buffer solution for reaction, a conventional PCR or real-time PCR buffer solution including Tris-HCl, KCl, (NH4) 2SO4, MgCl2, MgSO4 and the like can be suitably modified and used. The dNTPs include dATP, dTTP, dUTP, dGTP, and dCTP, and compositions including thio-dNTP, borano-dNTP, and methyl-dNTP can be used. The oligonucleotide can be used in a concentration ranging from 0.1 to 1 μM, and a suitable concentration for use can be easily determined by those skilled in the art.

There is provided a method of designing oligonucleotides of a target sequence amplification size of 50 to 1000 bp using the oligonucleotides of the present invention, in which amplification and real-time detection of the amplification sizes can be performed, so that the oligonucleotides are not limited to specific sizes but can be designed for candidate oligonucleotides of various sizes by selecting the sites where oligonucleotides can be designed. Since the oligonucleotide has a dual function of a primer and a probe, it provides an oligonucleotide and a design method which can confirm real-time amplification by attaching a reporter dye and a quencher molecule only to the target gene amplification site of two sites.

The oligonucleotides of the present disclosure can be used in forward or reverse locations, respectively, and provide a usable diversity in both locations.

The oligonucleotides of the present disclosure provide methods that can be analyzed individually or simultaneously by differently attaching reporter dyes to Fam, Texas Red, Cy5, Hex, Rox, Joe, Tamra, and Tet, etc. according to the target gene.

There are provided methods for the processes of the real-time PCR reactions using the oligonucleotides of the present disclosure and methods for the measurement.

The method is performed by repeating the denaturation, annealing, and extension steps. In addition, the fluorescence sequencing step is performed after the annealing and elongating steps, and then the fluorescence is measured to confirm the detection status of a specific gene in real time. Preferably, the fluorescent arraying step is performed at a temperature of 25 to 45° C. and the time is 1 second to 30 seconds, but is not limited thereto.

The present disclosure also provides a kit for individually or multi-simultaneously amplifying a specific gene for DNA and RNA of an infectious disease, hereditary disease, drug resistance, medication-refractory or susceptible specimen, in which the kit includes the oligonucleotide of the present disclosure as an active ingredient.

Effect

As described above, the oligonucleotide has two or more bubble structures including a mis-matched nucleotide sequence in the complementary base sequence as an oligonucleotide including a complementary base sequence by linking an Inosine linker at the 5' location. A pair of a reporter, which is a fluorescent substance, and a quencher, which is a quenching material, is placed in a base sequence complementary to the 5'-terminus of the primer, a mis-matched sequence, and a specific sequence of a target gene. It is possible to have a specificity equal to or higher than that of the Taqman system using three oligonucleotides only with two oligonucleotides by means of a method using a bi-functional oligonucleotide having both a primer and a probe function as an oligonucleotide having reactivity according to the annealing temperature of real-time PCR. It is possible to detect large-sized products up to 1000 bp in real time. This effect can be exerted on DNA polymerases with 5'3' exonuclease activity (+) or 5'3' exonuclease inactivity (−).

DESCRIPTION OF DRAWINGS

Figure 1:
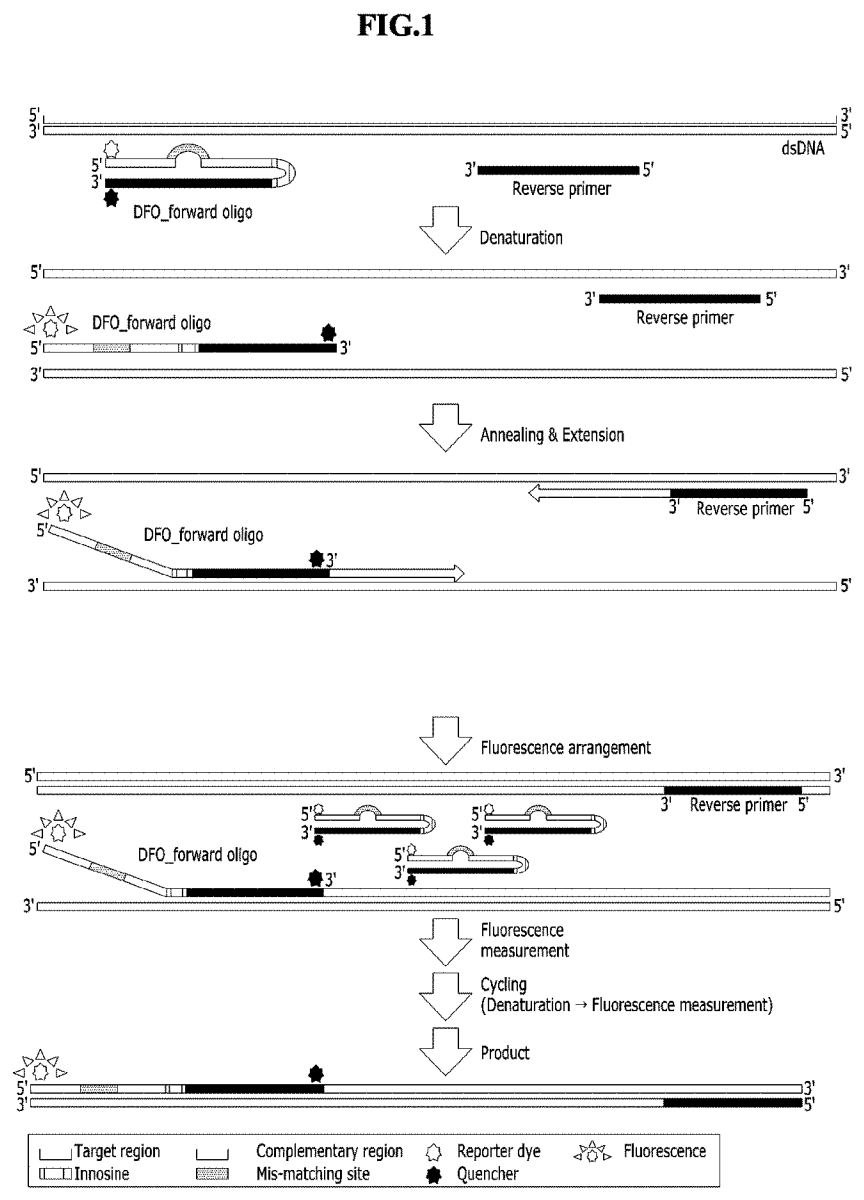

FIG. 1 is a sequential illustration of the oligonucleotide (DFO) structure of the present disclosure and a method for performing a real-time PCR using the same.

FIG. 3 illustrates a result of a real-time PCR by attaching a quencher molecule to the ninth base in the 5'-terminus direction from the 3'-terminus and the 3'-terminus of the oligonucleotide (DFO) of the present invention.

FIG. 4 illustrates a result of a real-time PCR by attaching a quencher molecule to the second and fourth bases from the 3'-terminus to the 5'-terminus direction of the oligonucleotide (DFO) of the present invention.

FIG. 10 illustrates a result of real-time PCR using DNA polymerases with 5'→3' exonuclease activity (+) or 5'→3' exonuclease inactivity (−) using the oligonucleotides (DFO) of the present invention, respectively.

FIG. 12 illustrates a result of a reaction using the oligonucleotide (DFO) of the present disclosure as a forward or reverse one and a real-time PCR using both of two oligonucleotides (DFO) as an oligonucleotide (DFO) of the present invention.

FIGS. 13 and 14 illustrate a result of a multiplex real-time PCR in which is simultaneously detected each target in a multiple manner compared with TaqMan system by attaching human beta-actin with Fam, HIV tat with Hex, and M13 with CY5, respectively in the oligonucleotide (DFO) of the present invention.

BEST MODE

Hereinafter, the present disclosure will be described in detail with reference to examples. However, the following examples are for illustrative purposes only and are not intended to limit the scope of the present invention.

Example 1: Analysis of the Light Emission Effect of the Oligonucleotide (DFO) of the Present Disclosure According to the Distance Between the Reporter Dye and the Quencher Molecule The oligonucleotides of the present disclosure place a complementary sequence at the 5'-terminus using a forward primer for a HIV t at gene and a human beta-actin gene and a reverse primer for a Rat GAPD gene of the prior method (Alexandre, V., et al., Nucleic Acid Research, 2008, 36:20, Ailenberg, M. and Silverman, M., BioTechniques, 2000, 29: 1018-1024) as a specific sequence of a target gene, and includes a mis-matched sequence in a complementary sequence.

In order to analyze the difference of the relative fluorescence unit (RFU) value between the reporter dye of DFO oligonucleotide and the quencher molecule, a reporter dye Fam was attached to the 5'-terminus. Based on this, the oligonucleotide was designed for SEQ ID NO: 2 (Fam01) located at the 3'-terminus of the double-stranded DFO oligonucleotide in terms of a quencher molecule location and SEQ ID NO: 7 (Fam02) located at the 2 mer at the 3'-terminus, SEQ ID NO: 8 (Fam04) located at the 4 mer at the 3'-terminus, SEQ ID NO: 11 (Fam05) located at the 5 mer at the 3'-terminus, SEQ ID NO: 9 (Fam07) located at the 7 mer at the 3'-terminus, SEQ ID NO: 10 (Fam08) located at the 8 mer at the 3'-terminus, SEQ ID NO: 3 (Fam09) located at the 9 mer at the 3'-terminus, SEQ ID NO: 4 (Fam15) located at the 15 mer at the 3'-terminus, SEQ ID NO: 5 (Fam17) located at the 17 mer at the 3'-terminus, and SEQ ID NO: 6 (Fam21) located at the 21 mer at the 3'-terminus. As a control group, SEQ ID NO: 1 (Control) was used for a TaqMan method.

The DFO of the present disclosure was subjected to denaturation with a double strand oligonucleotide to a single strand oligonucleotide to confirm the RFU value between the reporter dye and the quencher molecule distance. The DFO oligonucleotide was prepared in a reaction mixture of 0.5 μM, 0.2 mM dNTPs, 1.5 mM MgCl2 and the fluorescence was measured at 95° C. for 30 seconds, 65° C., 45° C., or 25° C. for 30 seconds. This was repeated 10 cycles.

Figure 2:
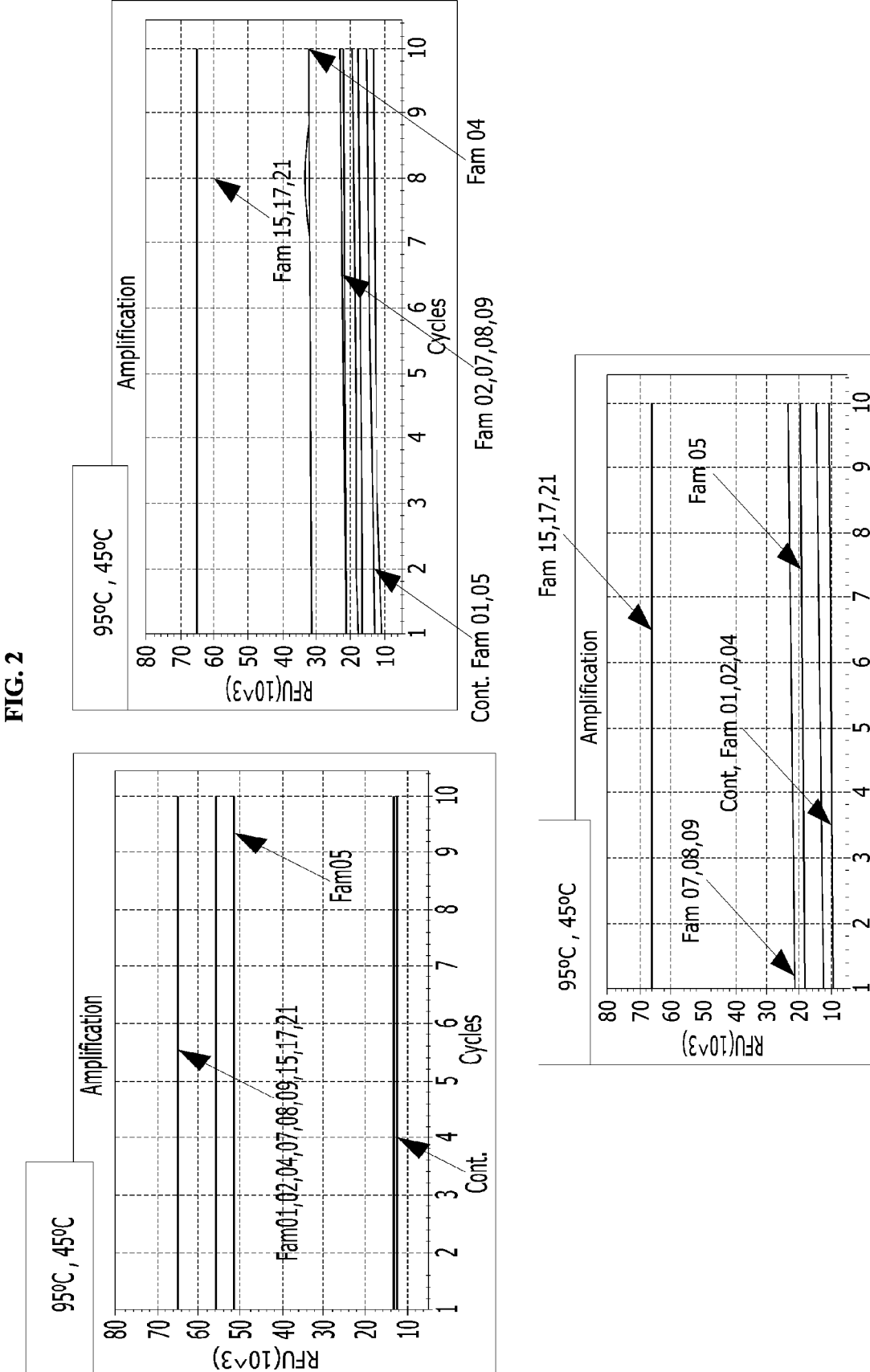
FIG. 2 illustrates a result of fluorescence measurement in which the reporter dye and the quaternary molecule in the double-stranded structure of the oligonucleotide (DFO) of the present disclosure are denatured to single strand at 65, 55 and 45° C. according to the number of mer (distance).

As a result, as illustrated in FIG. 2, the RFU value was found to be 53,000 to 65,000 as a whole as a result of measuring fluorescence after 65° C., and after 55° C., the RFU value decreased to 10,000 to 30,000, except Fam 15, Fam 17, Fam 21. At 25° C., the RFU value decreased to 10,000 to 20,000. Accordingly, at a temperature of around 65° C., the DFO oligonucleotides emit fluorescence in the form of a single strand as the distance between a reporter dye and a quencher molecule became farther away. As the temperature was lowered to 45° C. and 25° C., it was deformed in the form of a double stand so that the distance between a reporter dye and a quencher molecule became closer, and thus the amount of light emission decreased. In the case of Fam 15, Fam 17, and Fam 21, the distance between a reporter dye and a quencher became farther away even when it was deformed in a double strand, and thus the reporter dye continued to emit light.

Example 2: Analysis of a Real-Time PCR Effect According to the Location of a Quencher Molecule Near 3'-Terminus of DFO of the Present Invention In order to verify whether a realtime PCR was performed as the reporter dye or the quaternary molecule near the 3-terminus of the DFO of the present disclosure is located, a reporter dye was attached to the 5'-terminus and a quencher molecule is located at the 3'-terminus. SEQ ID NO: 2 and "T," which is the 2nd base of the 3'-terminus, were changed to innerdT in order to design SEQ ID NO: 7 to which BHQ1 was attached, "T," which is the 4th base of the 3'-terminus, was changed to innerdT in order to design SEQ ID NO: 8 to which BHQ 1, which is a quencher molecule, was attached, and "T," which is the 9th base ofthe 3'-terminus, was changed to innerdT in order to design SEQ ID NO: 3 to which BHQ1, which is a quencher molecule, was attached. In order to confirm the real-time PCR for the DFO oligonucleotide, the DFO oligonucleotide of SEQ ID NO: 2 or SEQ ID NO: 3 was used as a forward primer of the HIV tat gene. SEQ ID NO: 23 was used as a reverse primer. For the Rat GAPD gene, the forward primer used SEQ ID NO: 24 and the reverse primer used the DFO oligonucleotide SEQ ID NO: 7 and SEQ ID NO: 8. Each oligonucleotide set was added to 0.5 μM real-time PCR, and reaction mixtures of 0.2 mM dNTPs. 1× reaction buffer, and 0.5 U Taq DNA polymerase were prepared. Real-time PCR of the HIV tat gene was carried out by using HIV-1 isolate 10BR_PE064 (GI: 672918720, 5281-5700 bp) to prepare HIV tat plasmid DNA throu$^g$h gene synthesis Each 5 μl of 6.9, 0.6 ng/μl, 69, 6.9, 0.69 fg/μl of them was added to reaction mixtures to perform 40 cycles at 95° C. for 5 minutes (95° C. for 30 seconds, 55° C. for 30 seconds). As for the Rat GAPD gene, each 5 μl of 2, 02, 0.02 ng/μl of Rat genomic DNA (Clontech, Cat. No. 636404) was added to reaction mixtures to perform 40 cycles at 95° C. for 5 minutes (95° C. for 30 seconds, 60° C. for 30 seconds).

FIG. 3 confirms that an RU signal for the real-time PCR using SEQ ID NO: 2 to which a quencher molecule was attached to the DFO 3-terminus of the oligonucleotide set for detecting HIV tat gene and the 9th base of the 3-terminus rises to the same oblique line without regard to a template concertation. As for SEQ ID NO: 3, it was confirmed that Ct appears late as DFO decreases in template concentration. As for the RU signal, delta Rn exhibits SEQ ID NO NO: 3 of 8,000 RFU higher than that of SEQ ID NO: 2.

FIG. 4 illustrates a result of real-time PCR using SEQ ID NO.: 7 or SEQ ID NO.: 8 in which a quencher molecule was attached to the 2nd and 4th bases of DFO 3'-terminus of the oligonucleotide set for detecting Rat GAPD gene. It was detected that the delta Rn of the RFU signal was 12,500 and 10,000, respectively. A similar Ct was confirmed per concentration such that the DFO for the 2nd and 4th 3'-terminus of the quencher molecule was 22.43 Ct and 22.68 Ct at 10 ng/rxn, 26.22 Ct and 26.46 at 1 ng/rxn, and 29.73 Ct and 30.08 Ct at 0.1 ng/rxn, respectively.

As a result of FIGS. 3 and 4, when a quencher molecule or a reporter dye is attached to the 3'-terminus of the DFO oligonucleotide, fluorescence signal detection of the real-time PCR is inadequate. From the 2nd base at the 3'-terminus at minimum, the suitability for the real-time PCR was confirmed.

Example 3: Real-Time PCR Reaction Effect According to Single-Stranded Annealing Temperature According to Mis-Matching Sequence Number of DFO of the Present Invention The DFO of the present disclosure is formed as a double strand when the temperature is lower than a certain temperature in a single strand, which is controlled by mismatching sequence number. The forward primer of the set of oligonucleotides for detecting the beta-actin gene in human mRNA includes 4, 6, and 9 mis-matching sequence numbers, and at a temperature of around 65° C., 55° C. and 45° C., the DFO of SEQ ID NOs.: 12, 11 and 13 was designed so that a double strand is annealed to a single strand.

In human total RNA (stratagene, Cat. No. 750500), as for the cDNA synthesis for detecting beta-actin gene, 5 μl human total RNA (100 ng/μl) was added to the reaction mixture of 200 U MMLV Rtase, 1 μM of SEQ ID NO: 14 primer, 1× reaction buffer and 1 mM dNTPs for detection of beta-actin gene and reacted at 37° C. for 60 minutes and at 95° C. for 5 minutes.

In order to have a Taqman system as a control group to confirm the reaction effect according to an annealing temperature from a double strand to a single strand at the cycle temperature of the real-time PCR using the DFO, SEQ ID NO: 21 was used as a forward primer, SEQ ID NO: 14 used as a reverse primer, and SEQ ID NO: 25 was used as a taqman probe. As a test group, SEQ ID NO: 14 was used as a reverse primer and DFO of SEQ ID NO: 12, SEQ ID NO: 11 and SEQ ID NO: 13 according to each temperature was forwarded to prepare reaction mixtures of 0.3 μM, 0.2 mM dNTPs, 1× reaction buffer, and 0.5 U Taq DNA polymerase with each of an oligonucleotide set. 5 μl of total cDNA (total RNA. 25 ng/μl) was added and the control group was subjected to 40 cycles of 95° C. for 5 minutes (95° C. for 30 seconds and 60° C. for 30 seconds). The DFO oligonucleotide set was subject to 40 cycles of 95° C. for 5 minutes (95° C. for 30 seconds and 45° C. for 60 seconds).

Figure 5:
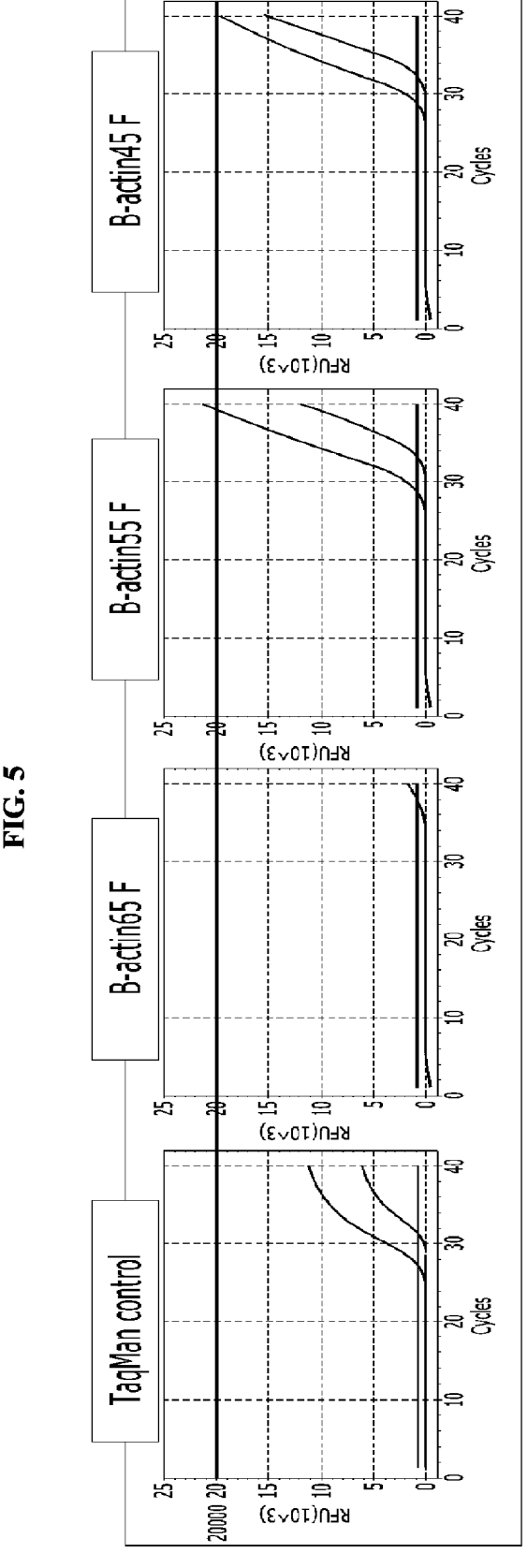
FIG. 5 illustrates a result of a real-time PCR according to the number of mis-matching sequences (4, 6, 9) located at the bubble site of the oligonucleotide (DFO) of the present invention.

As a result of FIG. 5, the control group, Taqman control, exhibits an RFU value of delta Rn of 12,500, no fluorescence signal was detected in the DFO oligonucleotide set of SEQ ID NO: 11 near the annealing temperature of B-actin 65 F of 65° C., and the set of DFO oligonucleotides of SEQ ID NO: 11 near the annealing temperature of 55° C. of B-actin 55 F and SEQ ID NO: 13 near the annealing temperature of 45° C., of B-actin 45 F has a delta Rn of 20,000 and exhibits a higher RFU signal value as compared to a Taqman control. These results indicate that the number of mis-matching sequences of DFO oligonucleotides are 4, and when annealing temperature is as high as 65° C., DFO released in single strand at a denaturation temperature is lowered to annealing and extension temperature. It could not be annealed to a target gene and is formed in a double strand, no real-time PCR was exhibited. In contrast, the number of mis-matching sequences is 6 or 9, and when the annealing temperature is as low as 55° C. and 45° C., the time for deformation to a double strand is shorter than an annealing temperature of 65° C. DFO. Thus, the target gene is annealed and an extension is performed to continuously form a single strand to detect fluorescence signals.

Example 4: Influence of Annealing and Extended Temperature Changes on Fixed Number of Mis-Matching Sequences of DFO of the Present Invention The efficiency of real-time PCR was analyzed by setting that mis-matching sequence number of DFO of the present disclosure is 6 and applying annealing and extension temperatures as a human nRNA beta-actin oligonucleotide set for designing DFO) oligonucleotide of SEQ ID NO: 11 and the reverse primer having an annealing temperature of 55° C. as SEQ ID NO: 14 as an annealing temperature of ±10° C.

In human total RNA (stratagene, Cat. No. 750500), as for the cDNA synthesis for detecting beta-actin gene, 5 μl human total RNA (100 ng/μl) was added to the reaction mixture of 200 U MMLV Rtase, 1 μM of SEQ 113 NO: 14 primer, 1× reaction buffer and 1 mM dNTPs for detection of beta-actin gene and reacted at 37° C. for 60 minutes and at 95° C. for 5 minutes.

As the oligonucleotide set and condition, a reaction mixture of 0.3 uM oligonucleotide, 0.2 mM dNTPs, 1× reaction buffer, and 0.5 U Taq DNA polymerase was prepared. After adding 5 μl of cDNA (total RNA 25 ng/μl), 40 cycles of 95° C. for 5 minutes (95° C. for 30 seconds, 65° C. or 55° C. or 45° C. for 30 seconds, 45° C. for 30 seconds) were performed.

Figure 8:
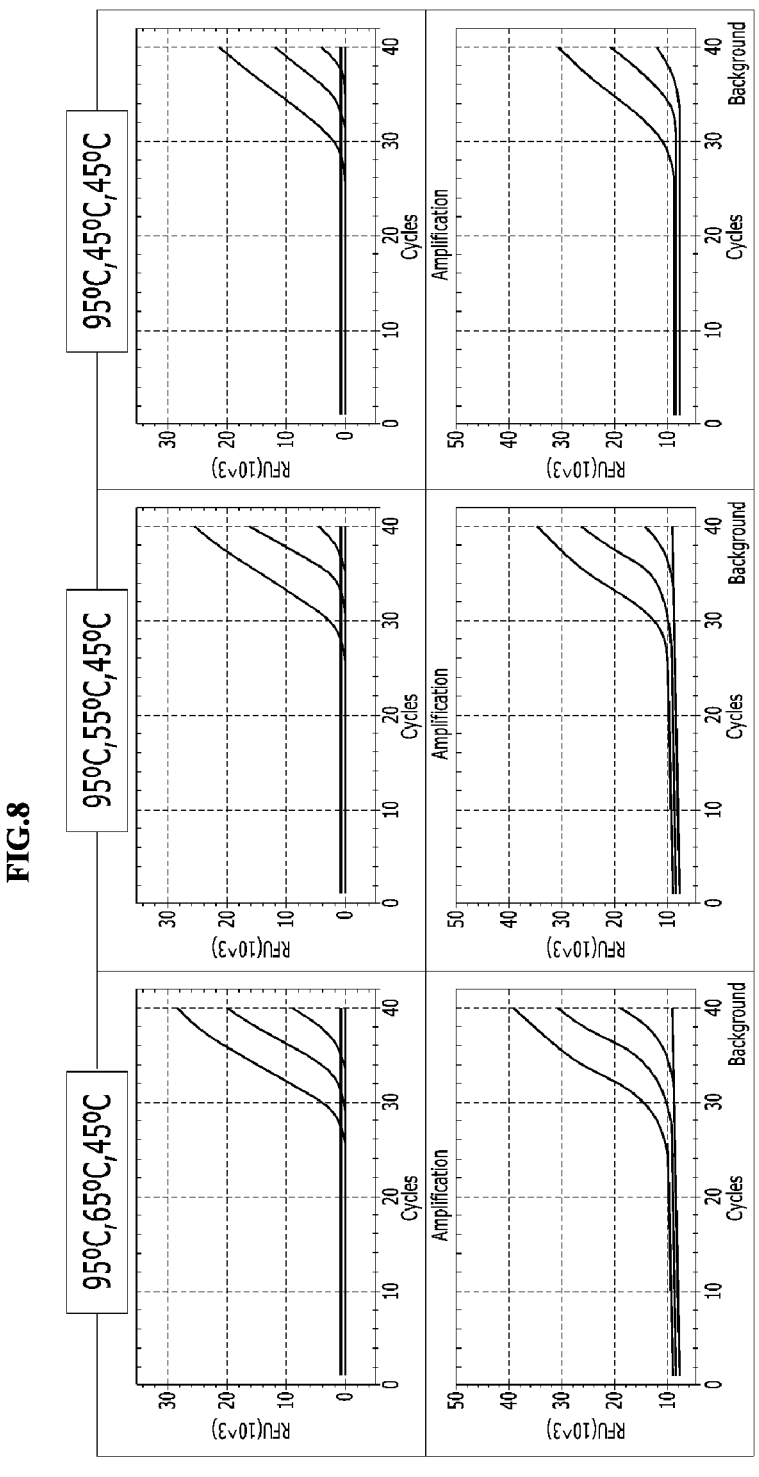
FIG. 8 relates to a result of real-time PCR at temperatures of 65, 55 and 45° C. for annealing and extension processes using the oligonucleotides (DFO) of the present invention.

As a result of FIG. 8, the delta Rn increased by RFU 3,000 with 10° C. rise as the temperature increased as compared to the annealing and extension temperatures of 45° C. Also, the Ct value was confirmed to be pulled around 1 Ct at a low concentration of 0.125 ng/rxn depending on the annealing and the extension temperature rise. Accordingly, when the temperature is higher than a certain temperature, it is transformed into single-stranded DFO to exhibit reactivity, and when the temperature is lower than a certain temperature, the reactivity is reduced and stopped.

Example 5: Addition of Fluorescence Measurement Step to the Cycle Condition of the DFO of the Present Disclosure and Effect According to Time Setting In order to set the DFO cycle condition of the present invention, as a set of oligonucleotides for human genomic DNA (Promega, G3041), DFO of SEQ ID NO: 11 and SEQ ID NO: 15 were used to prepare a reaction mixture of 0.3 μM, 0.2 mM dNTPs, 1× reaction buffer, 0.5 U Taq DNA polymerase. Human genomic DNA concentration was determined by performing 40 cycles of the number of performing initial denaturation at 95° C. for 5 minutes, denaturation (95° C.), annealing and extension (55° C.), and fluorescence measurement (45° C.) using 5 μl of 24.8, 2.48 and 0.248 ng/μl for 5 seconds/5 seconds/5 seconds, 10 seconds/10 seconds/10 seconds, 30 seconds/30 seconds/30 seconds, respectively.

Figure 6:
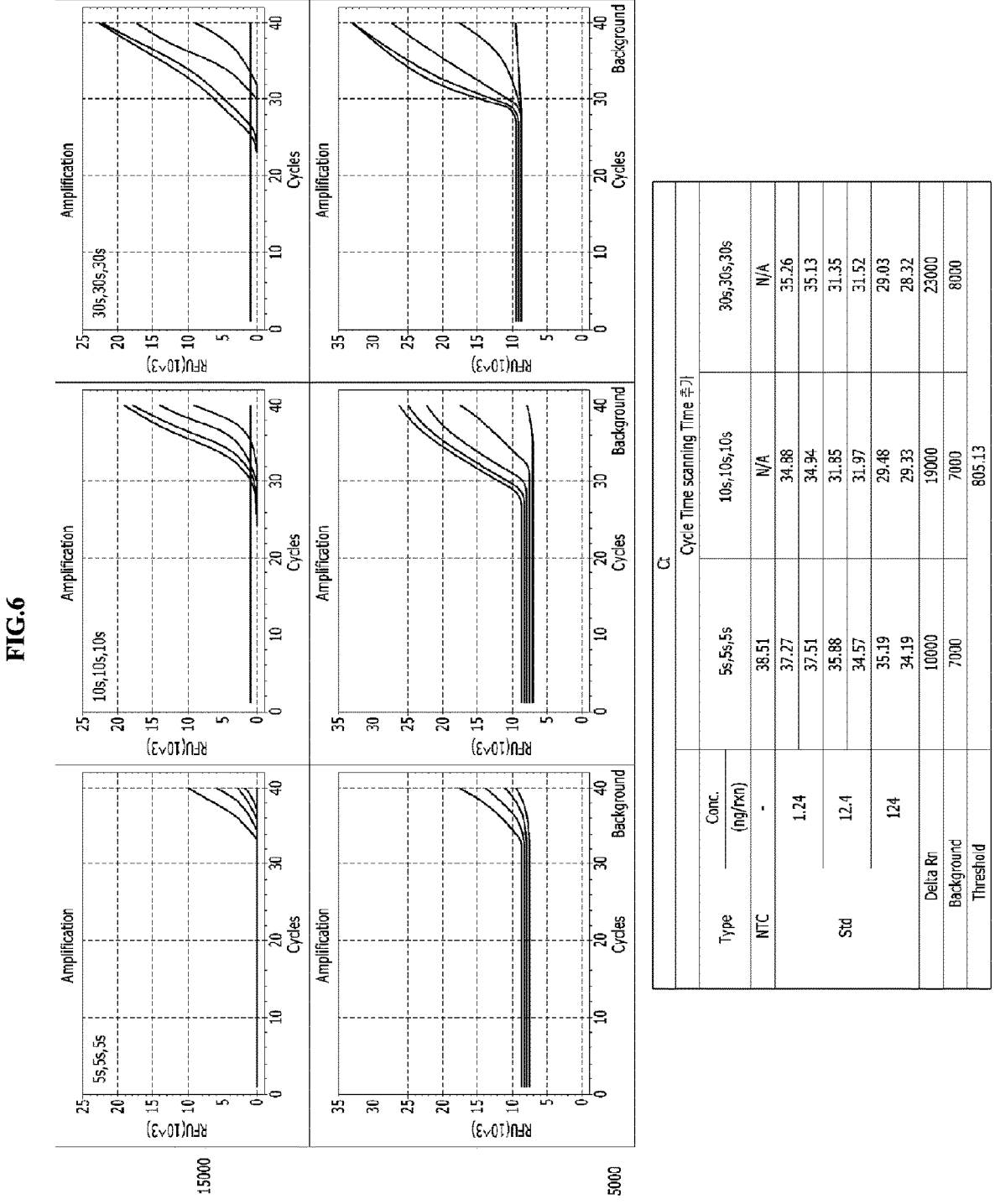
FIG. 6 illustrates a result of real-time PCR using the oligonucleotide (DFO) of the present disclosure according to the cycle time.

As a result of FIG. 6, the RFU value was 7,000 for the background of 5 seconds/5 seconds/5 seconds, 10 seconds/10 seconds/10 seconds, and the RFU value was similar to 8,000 for the 30 seconds/30 seconds/30 seconds. Ct values in proportion to concentration were not obtained in the case of 5 seconds/5 seconds/5 seconds, and the results of the Ct values in proportion to concertation in 10 seconds/10 seconds/10 seconds and 30 seconds/30 seconds/30 seconds were confirmed. The RFU of the delta Rn value of 30 seconds/30 seconds/30 seconds was exhibited to be higher than that of 10 seconds/10 seconds/10 seconds, but the Ct values exhibited similar results, and compared with 5 seconds/5 seconds/5 seconds, the RFU of the delta Rn of 10 seconds/10 seconds/10 seconds was exhibited to be 9,000 higher.

Figure 7:
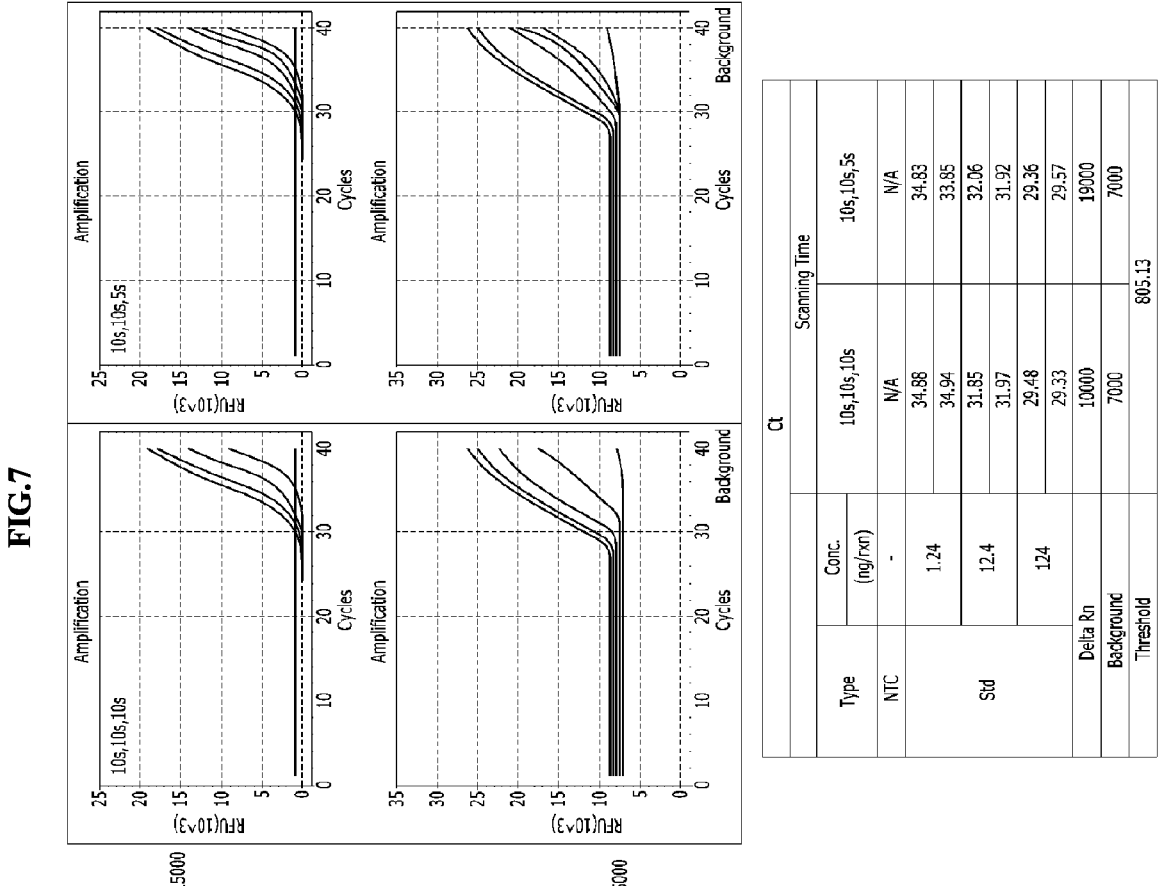
FIG. 7 illustrates a result of a method adding fluorescence measurement time (scanning time) for 5 and 10 seconds as a method of adding a denaturation process, which is a cycle condition to a real-time PCR using the oligonucleotide (DFO) of the present disclosure and adding a fluorescence measurement process to annealing and extension processes.

As a result, the RFU value of the same background and delta Rn was confirmed from the result of FIG. 7 which performs a test by reducing the fluorescence measurement time by 5 seconds under the 40 cycle condition of 10 seconds/10 seconds/10 seconds which exhibits a similar Ct condition and a stable RFU value. Ct value also exhibited a similar result. The reduction of fluorescence measurement time did not affect the real-time PCR using DFO.

Figure 9:
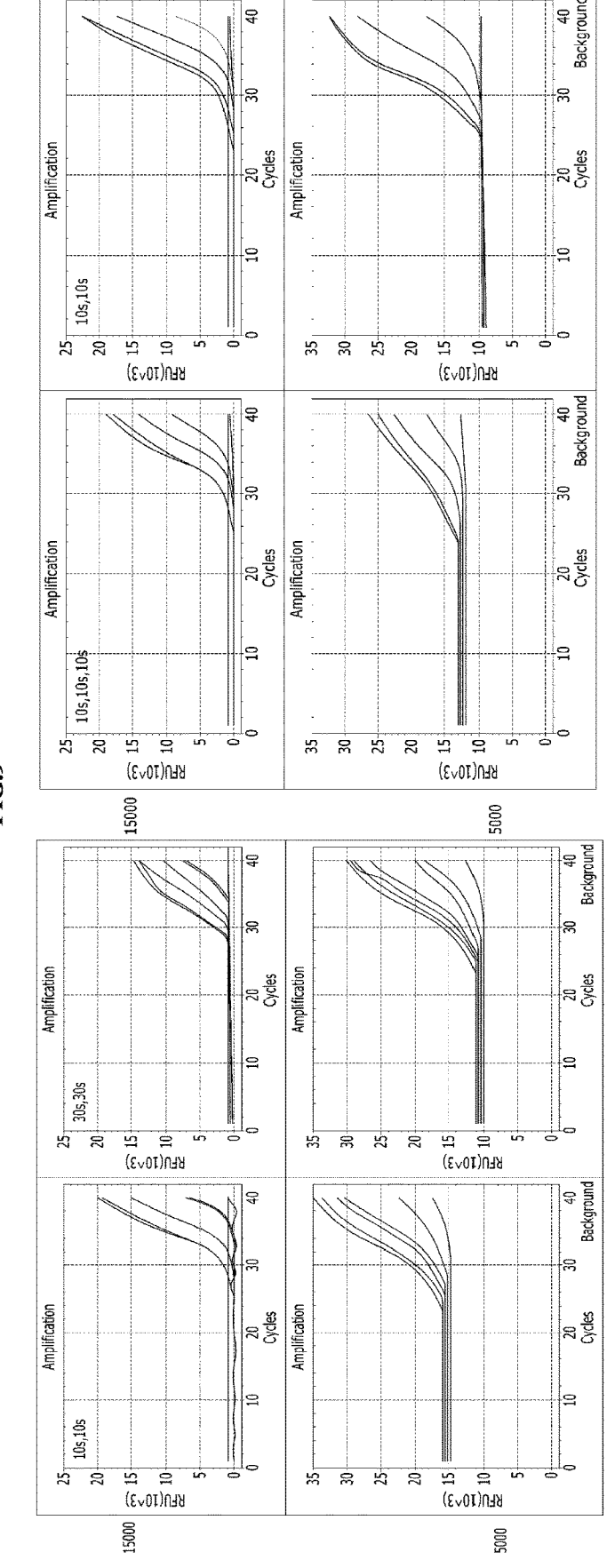
FIG. 9 illustrates a result of real-time PCR using the oligonucleotide (DFO) of the present disclosure according to a cycle condition including a fluorescence measurement process and a cycle condition not including the fluorescence measurement process.

As a result of FIG. 9, as a result of comparison of the conditions excluding and including the fluorescence measurement time, the fluorescence measurement time was included in 30 seconds/30 seconds/30 seconds compared to 30 seconds/30 seconds, and the RFU of the delta Rn value was exhibited to be 8,000 higher and the background was exhibited to be 3,000 lower. In 10 seconds/10 seconds/10 seconds compared to 10 seconds/10 seconds, the background was exhibited to be RFU 8,000 lower. The Ct value of including and excluding the fluorescence measurement time was similar.

Based on the above results, the effects were exhibited such that fluorescence measurement time was included to block fluorescence value detection of residual DFO of a single strand, fluorescence value could be measured only for the product amplified by binding with target gene, and background was lowered.

Example 6: Effect According to the Type of DNA Polymerase at the Time of Using DFO of the Present Invention In real-time PCR, the Taqman system uses DNA polymerase with 5'→3' exonuclease activity (+), and the reaction using intercalating dye such as SYBR green uses DNA polymerase with 5'→3' exonuclease activity (+) or 5'→3' exonuclease inactivity (−). In order to confirm the reactivity according to 5'→3' exonuclease activity (+) or inactivity (−) by using DFO of the present invention, 5 μl of cDNA (RNA concentration 2.5, 0.25, 0.025 ng/μl) synthesized with human total RNA was used. By using 0.3 μM of SEQ ID NOs.: 11 and 14, the reaction mixture of 0.2 mM dNTPs, 1× reaction buffer, 0.5 U DNA polymerase (5'→3' exonuclease activity (+) or inactive (−)) was prepared. 40 cycles were performed at 95° C. for 5 minutes (95° C. for 10 seconds, 55° C. for 10 seconds, and 45° C. for 5 seconds).

FIG. 10 illustrates the results of a real-time PCR reaction of 5'→3' exonuclease activity (+) or inactivity (−) with each DNA polymerase. The background is the same, in terms of delta Rn, DNA polymerase with 5'→3' exonuclease activity (+) was RFU 5,000 higher, but Ct was detected by drawing about 1.65 Ct of DNA polymerase with 5'→3' exonuclease inactivity (−). The DFO of the present disclosure was confirmed to have reactivity with DNA polymerase having 5'→3' exonuclease activity (+) or inactivity (−), respectively, and was highly sensitive to DNA polymerase having 5'→3' exonuclease inactivity (−). Accordingly, the real-time PCR can be performed using reporter dyes and quencher molecules such as Taqman system and DNA polymerase with 5'3' exonuclease inactivity (−) such as SYBR green.

Example 7: Effect of the DFO of the Present Disclosure According to the Amplification Sequence Size of a Specific Gene Desired for Real-Time Detection In the Taqman system, when the size of the sequence to be amplified exceeds 400 bp, it affects the reactivity of the real-time PCR, and the sequence for the three types of forward, reverse, and probe must be obtained from the sequence of the specific gene to be amplified. In the case of probes, the temperature design is limited to about 10° C. higher than forward and reverse. Accordingly, in order to confirm the reactivity according to the amplification sequence size using DFO of the present invention, DFO was used as forward (SEQ ID NO: 11). In order to confirm the reactivity according to the amplification size for reverse of 50 (SEQ ID NO: 16), 216 (SEQ ID NO: 14), 300 (SEQ ID NO: 17), 450 (SEQ ID NO: 18), 800 (SEQ ID NO: 19) and 1000 bp (SEQ ID NO: 20), the reaction mixture of 0.3 μM oligonucleotide, 0.2 mM dNTPs, 1× reaction buffer, 0.5 U Taq DNA polymerase was prepared, and subjected to 40 cycles of 95° C. for 5 minutes (95° C. for 20 seconds, 55° C. for 20 seconds, and 45° C. for 10 seconds).

Figure 11:
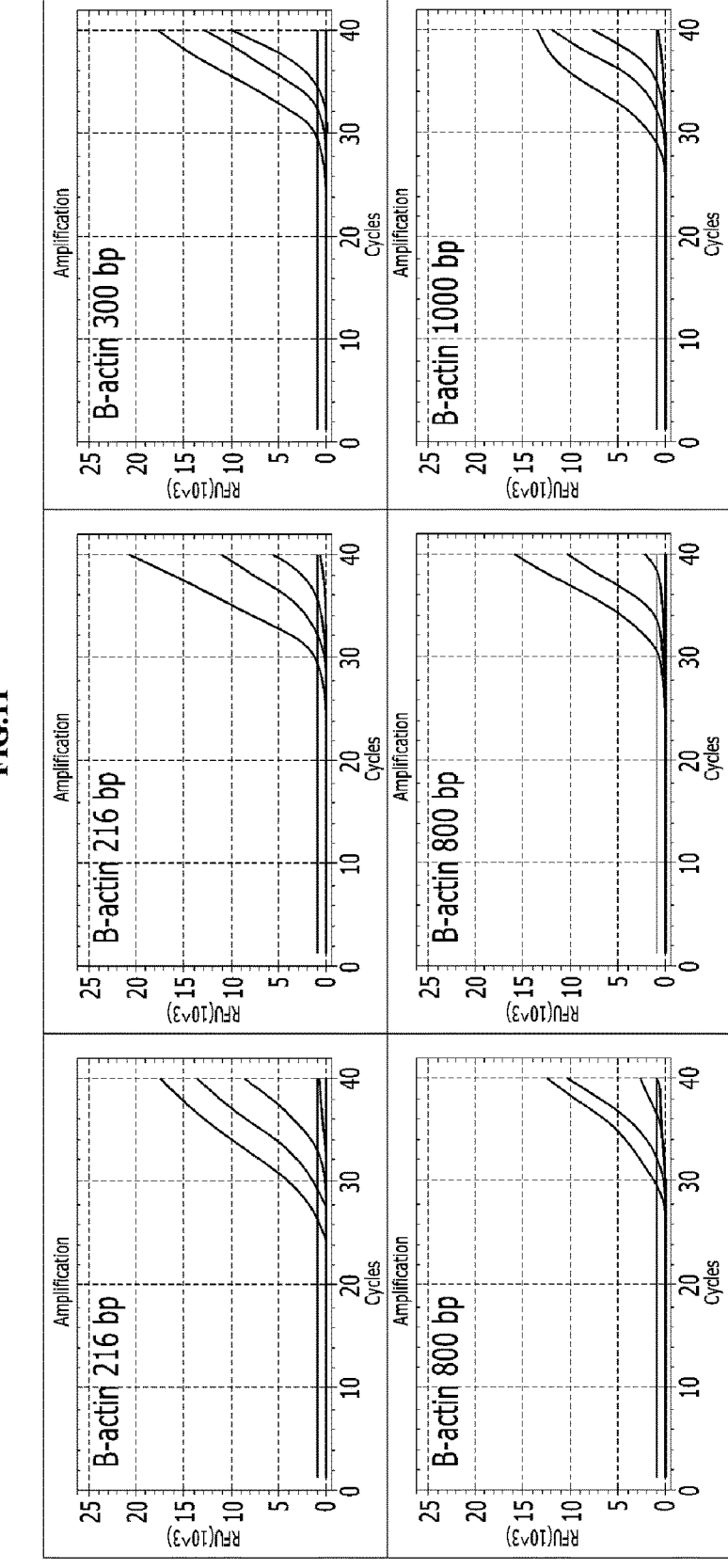
FIG. 11 illustrates a result of real-time PCR which applies the method of the present disclosure using the oligonucleotides (DFO) of the present disclosure and conventional primers with the size of the amplification products for real-time PCR of 50, 216, 300, 450, 800 and 1000 bp.

As illustrated in FIG. 11, when the same DFO was used as a forward and the reverse was designed according to the size, the Ct values of the different sizes compared to the Ct results of 50 bp were compared with each other. As a result, there was a difference of 0.74 Ct to 4.4 Ct, which was caused by the reactivity difference of reverse. There was no phenomenon that Ct was pushed according to the size, and the reactivity to 50 to 1000 bp amplification size was confirmed.

Example 8: Analysis of the Effects of Applying the DFO of the Present Disclosure to Forward and Reverse Positions, Respectively or as a Pair SEQ ID NO: 11 designing the DFO of the present disclosure as the forward primer location and SEQ ID NO: 22 designing the same sequence as SEQ ID NO: 14 as the reverse primer location are included in the real-tine PCR reaction, respectively or as a pair to confirm reactivity.

In human total RNA (stratagene, Cat No. 750500), as for the cDNA synthesis for detecting beta-actin gene, 5 μl human total RNA (100 ng/μl) was added to the reaction mixture of 200 U MMLV Rtase, 1 μM of SEQ ID NO: 14 primer, 1× reaction buffer and 1 mM dNTPs for detection of beta-actin gene and reacted at 37° C. for 60 minutes and at 95° C. for 5 minutes.

A set using the oligonucleotide used 0.304 of each of the three sets of oligonucleotides for a forward DFO of SEQ ID NO: 11 and reverse SEQ ID NO: 14, forward SEQ ID NO: 21, reverse DFO of SEQ ID NO: 22, forward DFO of SEQ ID NO: 11 and reverse DFO of SEQ ID NO: 22 to prepare a reaction mixture of 0.2 mM dNTPs, 1× reaction buffer, and 0.5 U Taq DNA polymerase, and 40 cycles of 95° C. for 5 minutes (95° C. for 30 seconds, 55° C. for 30 seconds, and 45° C. for 30 seconds) was performed.

As illustrated in FIG. 12, the delta Rn value was 12,500 higher in the result of performing the forward and reverse with DFO as compared to Taqman control. In the result of using forward and reverse DFO together, RFU was illustrated to be 15,000 higher. Ct values were similar to Taqman control.

Example 9: Analysis of Effects According to Multiplex Real-Time PCR Using DFO of the Present Invention For the multiplex real-time PCR reaction of human beta-actin mRNA, HIV tat gene and M13 bacteriophage, the DFO of the present disclosure was placed in the forward primer and the conventional primer was used as the reverse primer. SEQ ID NO: 11 and SEQ ID NO 14 including the reporter dye Fam and quencher molecule BHQ1 as a DFO oligo set were used for human beta-actin mRNA, SEQ ID NO: 26 and SEQ ID NO: 28 including the reporter dye HEX and the quencher molecule BHQ1 HIV were used for HIV tat gene, SEQ ID NO: 33 and SEQ ID NO: 31 including the reporter dye Cy5 and the quencher molecule BHQ2 were used for M13 bacteriophage for simultaneous detection. As a control group, SEQ ID NO: 21 and SEQ ID NO: 14 were used for the oligo set applying Taqman system, SEQ ID NO: 25 including the reporter dye Fam and quencher molecule BHQ1 were used for human beta-actin mRNA, SEQ ID NO: 27 and SEQ ID NO: 28, and SEQ ID NO: 29 including the reporter dye Hex and the quencher molecule BHQ1 were used for HIV tat gene, and SEQ ID NO NO: 30 and SEQ ID NO: 31 and SEQ ID NO: 32 including the reporter dye Cy5 and quencher molecule BHQ2 were used for M13 bacteriophage for simultaneous detection.

A reaction mixture of 0.2 mM dNTPs, 1× reaction buffer, and 0.5 U Taq DNA polymerase was prepared using the above oligo set at 0.3 μM, respectively. The reaction condition for the DFO oligo set was 95° C. for 5 minutes (95° C. for 30 seconds, 65° C. for 30 seconds, and 25° C. for 5 seconds) 40 cycles, and the reaction condition for TaqMan oligo set was 95° C. for 5 minutes (95° C. for 30 seconds and 65° C. for 30 seconds) 40 cycles.

In human total RNA (stratagene, Cat. No. 750500), for detection of a beta-actin gene, cDNA was synthesized by adding 5 μl human total RNA (100 ng/μl) to the reaction mixture of 200 U MMLV Rtase, 1 μM SEQ ID NO: 14 primer, 1× reaction buffer and 1 mM dNTPs and reacting at 37° C. for 60 minutes and 95° C. for 5 minutes. HIV tat plasmid DNA was prepared by gene synthesis in plasmid DNA using HIV-1 isolate 10BR_PE064 (GI: 672918720, 5281-5700 bp) as a template DNA for HIV tat gene amplification.

DNA was extracted from M13 bacteriophage (ATCC 15669-B1). For detection of the above three targets, the template (cDNA for human total RNA: HIV tat plasmid DNA: M13 bacteriophage DNA) (12.5 ng: 5×10^5 copies:

50 pg/test) and (1.25 ng: 5×10^4 copies: 5 pg/test) were used as the respective concentration for multiplex real-time PCR.

Figure 13:
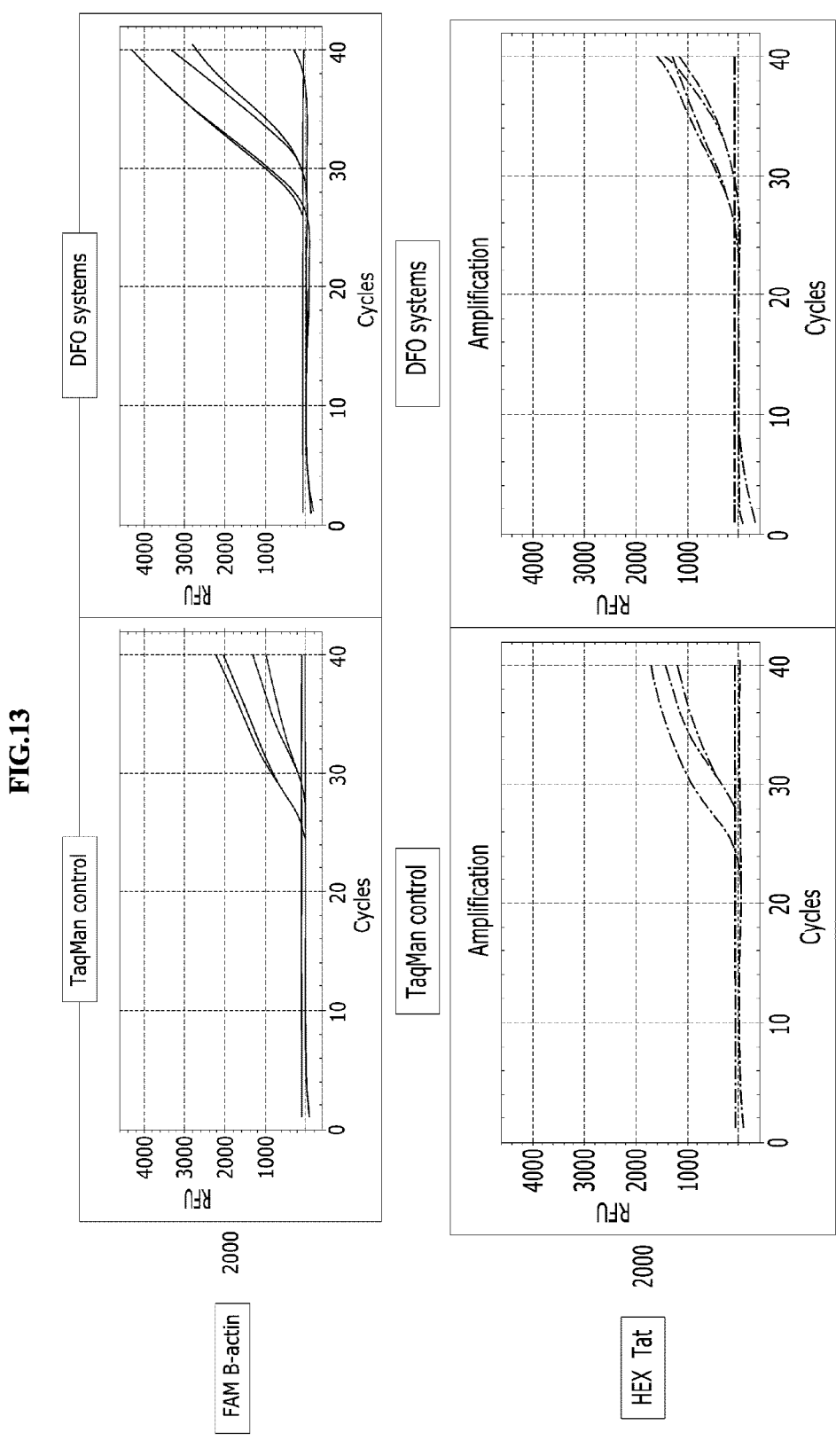
Figure 13:
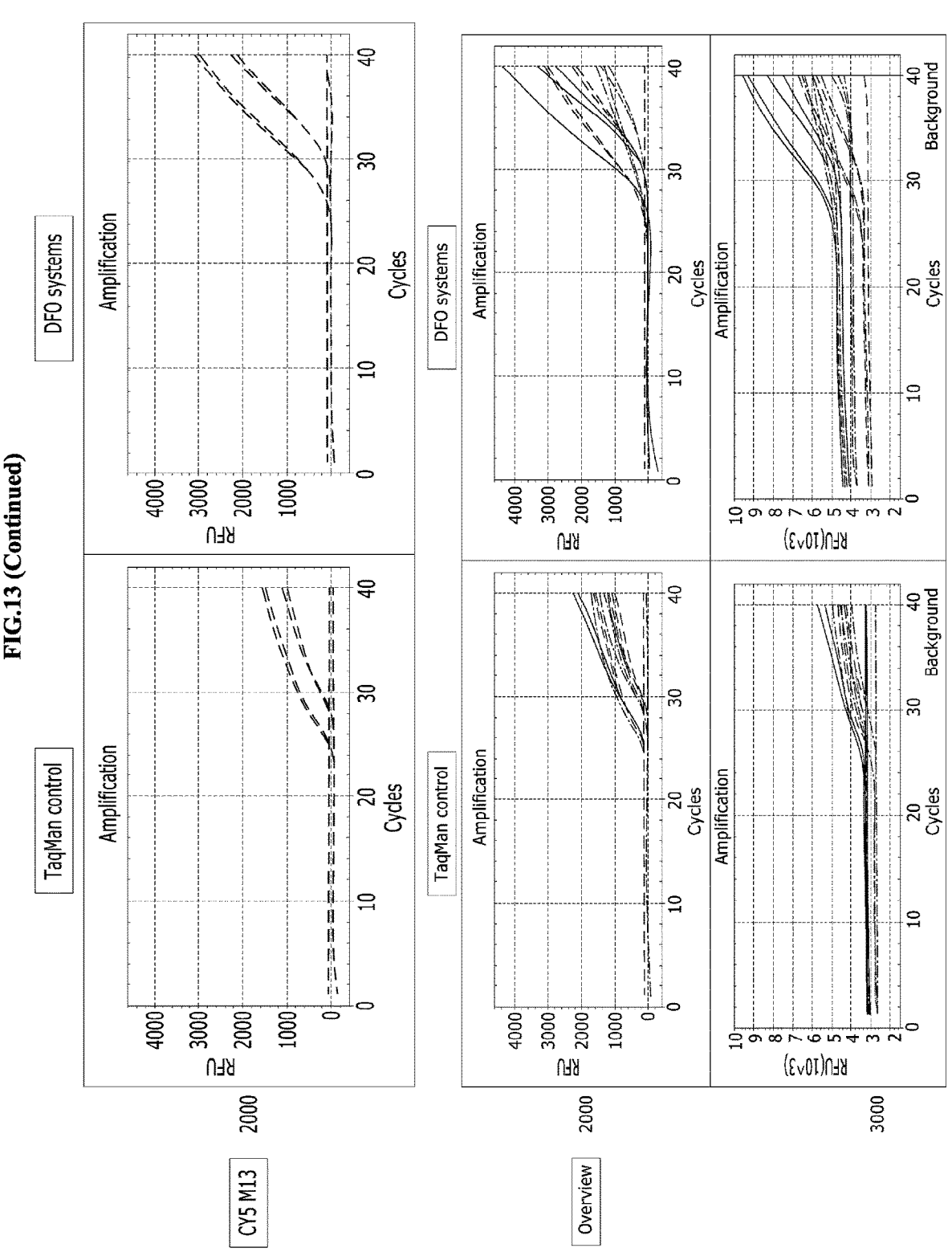

As illustrated in FIGS. 13 and 14, reporter dyes for three targets were altogether detected in the DFO system, like the TaqMan system, and Ct was confirmed to be similar. In the case of Delta Rn, the DFO system was 1.5 times higher than the TaqMan system.

---

What is claimed is:

1. A method for amplifying a target gene sequence having a length of 50 to 1000 base pairs and measuring a fluorescence signal in real time, the method comprising:

(a) providing a reaction mixture comprising a nucleic acid sample containing the target gene sequence, a polymerase, nucleotides, and an oligonucleotide;

(b) subjecting the reaction mixture to a nucleic acid amplification reaction under thermal cycling conditions comprising denaturation, annealing, and extension; and (c) monitoring the fluorescence signal from the reaction mixture in real time during the nucleic acid amplification reaction, wherein the oligonucleotide comprises:

a primer for amplifying the target gene sequence, a complementary sequence complementary to the primer, an inosine linker attached at its 3'-end to the 5'-terminus of the primer and at its 5'-end to the 3'-terminus of the complementary sequence, at least one mis-matched nucleotide within the complementary sequence to form at least one bubble structure in a double-stranded structure formed between the primer and the complementary sequence, and a pair of a reporter dye and a quencher molecule disposed within an oligonucleotide sequence, wherein, in a single-stranded state of the oligonucleotide, a distance between the reporter dye and the quencher molecule is at least 15 nucleotides, and in a double-stranded state of the oligonucleotide, the distance is 14 nucleotides or less, and wherein the oligonucleotide forms a double-stranded structure at temperatures below 40° C., and is denatured into a single-stranded structure at temperatures of 40° C. to 65° C.

2. The method according to claim 1, wherein the complementary sequence has two or more mis-matched nucleotide.

3. The method according to claim 1, wherein, for the pair of the reporter dyes and the quencher molecule in the single stranded structure, and a distance between the reporter dye and the quencher molecule is 15 mer or more.

4. The method according to claim 1, wherein the inosine linker is comprised of from 1 to 9 inosine nucleotides.

5. The method according to claim 1, wherein the oligonucleotide is used in a forward or reverse location for gene amplification and a real-time PCR.

6. The method according to claim 1, wherein the oligonucleotide is one of SEQ ID NOs: 3, 7 to 13, SEQ ID NO: 22, SEQ ID NO: 26, or SEQ ID NO: 33.

7. The method according to claim 1, wherein the oligonucleotide comprises one to four bubble structures.

* * * * *